(12) United States Patent
Millan et al.

(10) Patent No.: US 7,888,372 B2
(45) Date of Patent: Feb. 15, 2011

(54) COMPOSITIONS AND METHODS FOR MODULATING BONE MINERAL DEPOSITION

(75) Inventors: Jose Luis Millan, San Diego, CA (US); Robert Terkeltaub, San Diego, CA (US)

(73) Assignees: National Institutes of Health (NIH), Bethesda, MD (US); The Regents of the University of California, Oakland, CA (US)

( * ) Notice: Subject to any disclaimer, the term of this patent is extended or adjusted under 35 U.S.C. 154(b) by 2191 days.

(21) Appl. No.: 10/426,005

(22) Filed: Apr. 28, 2003

(65) Prior Publication Data

US 2004/0023916 A1    Feb. 5, 2004

Related U.S. Application Data

(63) Continuation-in-part of application No. 10/104,482, filed on Mar. 22, 2002, now abandoned.

(60) Provisional application No. 60/278,197, filed on Mar. 23, 2001.

(51) Int. Cl.
*A01N 43/42* (2006.01)
*A01N 37/12* (2006.01)

(52) U.S. Cl. ................................ 514/310; 514/565

(58) Field of Classification Search .................. 514/310
See application file for complete search history.

(56) References Cited

U.S. PATENT DOCUMENTS

| 4,238,507 | A | * | 12/1980 | Umezawa et al. | ........... 514/567 |
| 5,773,226 | A | | 6/1998 | Millan | |
| 5,948,630 | A | * | 9/1999 | Singh et al. | ................ 435/21 |
| 6,290,952 | B1 | * | 9/2001 | Poelstra et al. | ................ 424/94 |

OTHER PUBLICATIONS

Kathryn Elizabeth McDougall, Alkaline Phosphatase Isozyme Expression in Preattachment Bovine Embryos; The University of Guelph, A Thesis Presented to the Faculty of Graduate Studies of the University of Guelph; Oct. 1998; pp. 27,83,86-87,89,92,94,100,150,152,164, Abstract, Title Page, and Acknowledgements.*

Sugawara et al. Necessity of Enzymatic Activity of Alkaline Phosphatase for Mineralization of Osteoblastic Cells, The Japanese Journal of Pharmacology, vol. 88 (2002), No. 3, pp. 262-269, printed pp. 1 and 2, especially p. 1).*

Garba et al., Alkaline Phosphatase inhibition by levamisole prevents 1, 25-dihydroxyvitamin D3-stimulated bone mineralization in the mouse., Calcif Tissue Int. (1986); 38(5):296-302, printed pp. 1 and 2, especially p. 1).*

Linde et al., Inhibition Studies of Alkaline Phosphatases in Hard Tissue-Forming Cells, The Journal of Histochemistry and Cytochemistry, (1975), vol. 23, No. 5, pp. 342-347.*

Lin et al., L-Homoarginine: An Organ-Specific, Uncompetitive Inhibitor of Human Liver and Bone Alkaline Phosphatases, The Journal of Biological Chemistry, (1972) vol. 247, No. 10, pp. 3082-3087).*

Whisnant et al., Capillary electrophoretic analysis of alkaline phosphatase inhibition by theophylline, Electrophoresis, (2000); 21(7): 1341-8, printed p. 1).*

Beertsen, et al., "Root development in mice lacking functional tissue on non-specific aklaline phosphatase gene: Inhibition of acellular cementum formation," *Journal of Dental Research*, (Jun. 1999) vol. 78, Issue 6, pp. 1221-1227.

Lotz, et al., "Interleukin 1-Beta suppresses transforming growth factor-induced inorganic pyrophosphate (PPi) production and expression of the PPi-generating enzyme PC-1 in human chondrocytes," *Proc. Natl. Acad. Sci. USA*, (Oct. 1995), vol. 92, pp. 1221-1227.

* cited by examiner

*Primary Examiner*—Sreeni Padmanabhan
*Assistant Examiner*—Timothy E Betton
(74) *Attorney, Agent, or Firm*—Pabst Patent Group LLP

(57) ABSTRACT

The key function of TNAP in bone is degradation of PPi to remove this mineralization inhibitor and provide free phosphate for apatite deposition. PC-1 is a direct antagonist of TNAP function. ANK also antagonizes TNAP-dependent matrix calcification. Specifically, the activity of PC-1 inhibits initial MV apatite deposition, but ANK inhibits propagation of apatite outside the MVs. Furthermore, loss of function of the two distinct skeletal TNAP antagonists, PC-1 and ANK, ameliorates TNAP deficiency-associated osteomalacia in vivo. Conversely, the hyperossification associated with both PC-1 null mice and ANK-deficient (ank/ank) mice is ameliorated by deficiency of TNAP in vivo.

7 Claims, 7 Drawing Sheets

FIG. 1A

FIG. 1B 1:16 (ttpp)

FIG. 1C 1:4 (ttpp)

FIG. 2A

FIG. 2B 1:16 (ttaa)

FIG. 2C 1:4 (ttaa)

COMPOSITIONS AND METHODS FOR MODULATING BONE MINERAL DEPOSITION

PRIORITY APPLICATION INFORMATION

This application is a continuation-in-part of and claims priority to U.S. application Ser. No. 10/104,482, filed Mar. 22, 2002 now abandoned, and U.S. provisional application Ser. No. 60/278,197, filed Mar. 23, 2001.

STATEMENT AS TO FEDERALLY SPONSORED RESEARCH

The invention was made with Government support under NIH 5P01 AGO07996-110002; NIH 5R01 CA042595-15; NIH 5R01 DE012889-02 and 5RO1 AR47908-01A1. The Government may have certain rights in the invention.

FIELD OF THE INVENTION

This invention relates to the field of modification of bone mineral deposition.

BACKGROUND OF THE INVENTION

Osteoblasts mineralize the pericellular matrix by promoting initial formation of crystalline hydroxyapatite in the sheltered interior of membrane-limited matrix vesicles (MVs) and by modulating matrix composition to further promote propagation of apatite outside of the MVs. Three molecules present in osteoblasts have been identified by means of gene knock-out models as affecting the controlled deposition of bone mineral, i.e., alkaline phosphatase (TNAP); PC-1 (or Npps, a nucleoside triphosphate pyrophosphate hydrolase isozyme, NTPPPH) and ANK, a multipass membrane protein that appears to serve as an anion channel. Our inactivation of the mouse TNAP gene led to the development of a model of Infantile Hypophosphatasia characterized by undermineralization of bone (osteomalacia). Inactivation of the PC-1 gene causes systemic hyperossification and skeletal and extraskeletal apatite deposition. Moreover, ANK-deficient ank/ank mutant mice have recently been described as developing a phenotype remarkably similar to that of the PC-1 null mice.

A deficiency in the TNAP isozyme causes hypophosphatasia, the study of which has provided the best evidence of the importance of TNAP for bone mineralization. TNAP is the only tissue-nonrestricted isozyme of a family of four homologous human. AP genes (EC. 3.1.3.1) (Millán and Fishman, Crit. Rev. Clin. Lab. Sci. 32:1-39, 1995). Expressed as an ecto-enzyme transported to the osteoblast plasma membrane and anchored via a phosphatidylinositol glycan moiety, TNAP has been demonstrated to play an essential physiological role during osteoblastic bone matrix mineralization (Whyte, Endocrine Rev. 15:439-461, 1994; Narisawa et al., Dev. Dynamics 208:432-446, 1997; Zurutuza et al., Hum. Mol. Genet. 8:1039-1046, 1999). Specifically, defective bone mineralization (osteomalacia) occurs in TNAP deficiency (hypophosphatasia) (Whyte, Endocrine Rev. 15:439-461, 1994). The severity of hypophosphatasia is variable and modulated by the nature of the TNAP mutation (Henthorn et al., Proc. Nat. Acad. Sci. U.S.A. 89:9924-9928, 1992; Fukushi et al., Biochem. Biophys. Res. Comm. 246:613-618, 1998; Shibata et al., J. Biochem. 123:968-977, 1998; Narisawa et al., Dev. Dynamics 208:432-446, 1997; Zurutuza et al., Hum. Mol. Genet. 8:1039-1046, 1999; Di Mauro et al., J. Bone Min. Res. 17: 1383-1391, 2002). Unlike most types of rickets or osteomalacia, neither calcium nor inorganic phosphate levels in serum are subnormal in hypophosphatasia. In fact hypercalcemia and hyperphosphatemia may exist, and hypercalciuria is common in infantile hypophosphatasia (Whyte, "Hypophosphatasia," In: The Metabolic and Molecular Bases of Inherited Disease, ed. Scriver et al., McGraw-Hill Inc., New York, pp. 4095-4112, 1995). The clinical severity in hypophosphatasia patients varies widely. The different syndromes, listed from the most severe to the mildest forms, are: perinatal hypophosphatasia, infantile hypophosphatasia, childhood hypophosphatasia, adult hypophosphatasia, odontohypophosphatasia and pseudohypophosphatasia (Whyte, "Hypophosphatasia," In: The Metabolic and Molecular Bases of Inherited Disease, ed. Scriver et al., McGraw-Hill Inc., New York, pp. 4095-4112, 1995). These phenotypes range from complete absence of bone mineralization and stillbirth to spontaneous fractures and loss of decidual teeth in adult life.

Physiologic bone matrix mineralization is hypothesized to be dependent on the availability of Pi released from a variety of substrates by certain MV ecto-enzymes (Anderson, Clin. Orthopaed. Rel. Res. 314:266-280, 1995; Hsu and Anderson, J. Biol. Chem. 271:26383-26388, 1996). For example, ATP is hypothesized to drive the initiation of calcification by MVs in vivo, and a specific bone and cartilage ATPase appears to be responsible for the ATP-dependent calcium and Pi-depositing activity of bone and cartilage-derived MVs in vitro (Hsu and Anderson, 1996; Pizauro et al., 1998). Skeletal TNAP can catalyze Pi release from ATP (Hsu and Anderson, J. Biol. Chem. 271:26383-26388, 1996; Pizauro et al., Biochim. Biophys. Acta 1368:108-114, 1997), TNAP catalyzes several transphosphorylation reactions (Whyte, Endocrine Rev. 15:439-461, 1994) and TNAP can also function as a pyrophosphatase (Moss et al., Biochem. J. 102:53-57, 1967; Rezende et al., Biochem. J. 301:517-522, 1994). Although TNAP does not appear to dephosphorylate membrane proteins (Fedde et al., J. Cell. Biochem. 53:43-50, 1993), TNAP has been hypothesized to modulate bridging of MVs to matrix collagen (Whyte, Endocrine Rev. 15:439-461, 1994; Henthorn et al., "Acid and alkaline phosphatases," In: Principles of Bone Biology, eds. Seibel et al., Academic Press, pp. 127-137, 1999). TNAP has been demonstrated to bind calcium (de Bernard et al., J. Cell. Biol. 103:1615-1623, 1986). Moreover, TNAP degrades at least three phosphocompounds, i.e., phosphoethanolamine, pyridoxal 5' phosphate, and PPi, that accumulate endogenously in hypophosphatasia (Whyte et al., "Hypophosphatasia," In: The Metabolic and Molecular Bases of Inherited Disease, ed. Scriver et al., McGraw-Hill Inc., New York, pp. 4095-4112, 1995). The central function or functions of TNAP in conditioning mineralization have not been completely defined (Whyte, Endocrine Rev. 15:439-461, 1994). Importantly, aberrant localization of TNAP can occur, including defective transport of TNAP to the plasma membrane associated with hypophosphatasia (Fedde et al., Am. J. Hum. Genet. 47: 767-775, 1990; Fedde et al., Am. J. Hum. Genet. 47:776-783, 1990; Fukushi et al., Biochem. Biophys. Res. Comm. 246:613-618, 1998). The ability of TNAP to hydrolyze PPi to Pi (Whyte et al., "Hypophosphatasia," In: The Metabolic and Molecular Bases of Inherited Disease, ed. Scriver et al., McGraw-Hill Inc., New York, pp. 4095-4112, 1995) has been hypothesized to be central to the ability of TNAP to promote osteoblastic mineralization (Anderson et al., Am. J. Pathol. 151:1555-1561, 1997; Whyte, Endocrine Rev. 15:439-461, 1994, Pizauro et al., Biochim. Biophys. Acta 1368:108-114, 1998). A major action of PPi is to suppress both the deposition and propagation of hydroxyapatite crystals in vitro (Johnson et al., J. Bone Miner. Res.

14:883-892, 1999; Johnson et al., *Arthritis Rheum.* 42:1986-1997, 1999; Meyer, *Arch. Biochem. Biophys.* 231:1-8, 1984). Thus, critically timed removal or exclusion of PPi at sites of mineralization appears to be necessary for active crystal deposition to proceed (Johnson et al., *J. Bone Miner. Res.* 14:883-892, 1999; Johnson et al., *Arthritis Rheum.* 42:1986-1997, 1999; Meyer, *Arch. Biochem. Biophys.* 231:1-8, 1984). Since TNAP functions as a PPi-ase in vitro (Moss et al., *Biochem. J.* 102:53-57, 1967; Rezende et al., *Biochem. J.* 301:517-522, 1994), the finding that NTPPPH activity is normal in fibroblasts from hypophosphatasia patients further supported the hypothesis that accumulation of PPi in this disease is the result of defective degradation (Caswell et al., *J. Clin. Endocrinol. Metab.* 63:1237-1241, 1986). In vitro studies have shown that PPi promotes formation of amorphous calcium phosphate, while the subsequent transformation into hydroxyapatite and growth of hydroxyapatite crystals are inhibited (Caswell et al., *Crit. Rev. Clin. Lab. Sci.* 28:175-232, 1991). Plasma Cell Membrane Glycoprotein-1 (PC-1) is a nucleotide triphosphate pyrophosphate hydrolase (NTPPPH) isozyme expressed by cultured osteoblastic cells (Goding et al., *Immunol. Reviews* 161:11-26, 1998; Johnson et al., *J. Bone Miner. Res.* 14:883-892, 1999; Solan et al., *J. Bone Miner. Res.* 11:183-192, 1996). NTPPPH activity is a property of several members of a phosphodiesterase nucleotide pyrophosphatase (PDNP) family of ecto-enzymes that also includes B10 and autotaxin (Johnson et al., *J. Bone Miner. Res.* 14:883-892, 1999; Johnson et al., *Arthritis Rheum.* 42:1986-1997, 1999). PC-1 expression, and the extent of PC-1 distribution to MVs, are regulated by certain growth factors and calciotropic hormones, including TGFα, bFGF, and 1,25 dihydroxyvitamin D3 (Bonewald et al., *Bone and Mineral* 17:139-144, 1992; Johnson et al., *J. Bone Miner. Res.* 14:883-892, 1999; Johnson et al., *Arthritis Rheum.* 42:1986-1997, 1999; Oyajobi et al., *J. Bone Miner. Res.* 9:99-109, 1994; Oyajobi et al., *J. Bone Miner. Res.* 9:1259-1269, 1994; Solan et al., *J. Bone Miner. Res.* 11:183-192, 1996). Osteoblast-derived MV PC-1 appears to function directly to increase MV fraction PPi content and to restrain mineralization by isolated MVs in vitro (Johnson et al., *J. Bone Miner. Res.* 14:883-892, 1999; Johnson et al., *Arthritis Rheum.* 42:1986-1997, 1999). In this regard, a two- to four-fold increase in osteoblast PC-1 expression decreases, by greater than 80%, the amount of hydroxyapatite deposited in the pericellular matrix of osteoblasts in vitro (Johnson et al., *J. Bone Miner. Res.* 14:883-892, 1999; Johnson et al., *Arthritis Rheum.* 42:1986-1997, 1999). On the other hand a dysregulated increase in chondrocyte PPi production is a central feature of idiopathic chondrocalcinosis (or primary calcium pyrophosphate dihydrate, CPPD, crystal deposition disease) whose prevalence appears to be greater than 15% at age 65 and rises progressively with age. Mean cartilage PPi-generating NTPPPH activity doubles, promoting PPi supersaturation that stimulates CPPD crystal deposition in the pericellular matrix of chondrocytes in articular cartilage and fibrocartilaginous menisci. Interestingly, it appears that both up-regulation as well as inactivation of PC-1 leads to osteoarthritic disease albeit by different molecular mechanisms. The role of PC-1 on mineralization have been confirmed to be physiologically significant in ttw/ttw (formerly known as "tiptoe walking Yoshimura") mice (Okawa et al., *Nature Genet.* 19:271(1998), which are homozygous for a naturally occurring PC-1 truncation mutation. In early life, ttw/ttw mice develop not only progressive ossification of spinal and peripheral joint ligaments but also articular and meniscal cartilage calcification.

The ankylosis protein (ANK) has a role in suppressing mineralization by contributing to the extracellular supply of $PP_i$. However, unlike PC-1, ANK appears to function as a transmembrane $PP_i$-channeling protein, allowing $PP_i$ molecules to passage through the plasma membrane from the cytoplasm to the outside of the cell (Ho et al., *Science* 289: 265-269, 2000; Nümberg et al., *Nat. Genet.* 28: 37-41, 2001). ANK protein is detectable in many tissues, yet its expression is particularly strong in the cartilage of joints (Ho et al., *Science* 289: 265-269, 2000). Cell surfaces of osteoblasts and chondrocytes appear to be abundant in ANK protein, but in contrast to PC-1 and TNAP, it is not present in the membranes of MVs. The discovery of the ANK protein was recently accomplished by identifying the gene in a naturally occurring mutant mouse strain that had characteristics of progressive ankylosis, thereupon the designation ank mice (Ho et al., *Science* 289: 265-269, 2000). The ANK gene in this mutant mouse line has a nonsense mutation in the open reading frame that translates into a premature stop codon and a truncated non-functional protein. ank/ank mice develop hydroxyapatite crystals in articular surfaces and synovial fluids. ank/ank mice display pathological abnormalities that mimic several arthritic diseases, including ectopic calcification, cartilage erosion and osteophyte formation seen in osteoarthritis, and vertebral fusion observed in ankylosis spondylitis patients (Sweet and Green, *J. Hered.* 72: 87-93, 1981; Hakim et al., *Arthr. Rheum.* 27: 1411-1420, 1984; Sampson and Davis, *Spine* 13: 650-654, 1988; Mahowald et al., *J. Rheumatol.* 16: 60-66, 1989).

The clinical linkages of increased PPi production and NTPPPH activity to chondrocalcinosis are well-recognized. Moreover, the association of both PC-1 deficiency and defective ANK function with articular cartilage degeneration and apatite deposition in mice further links basic studies of PC-1 and ANK function and PPi metabolism to clinical arthritic disease. The perispinal ligamentous ossification of both PC-1 deficient and ank/ank mice is noteworthy, because it is modulated by unrestrained growth, and by chondrocytic and osteoblastic metaplasia of perispinal ligament fibroblasts and of periosteum, respectively (Sali et al., "Germline deletion of the nucleoside triphosphate (NTPPPH) plasma cell membrane glycoprotein (PC-1) produces abnormal calcification of periarticular tissues," In: *Conference Proceedings: Second International Symposium on Ecto-ATPases and Related Ectonucleotidases*; ed. Vanduffel and Lemmens, Shaker Publishing BV, Maastricht, Netherlands, pp. 267-282, 1999; Okawa et al., *Nature Gen.* 19:271-273, 1998; Ho et al., *Science* 289:265-270, 2000; Krug et al., *J. Rheumatol.* 27:1257-1259, 2000).

Osteopontin (OPN), first identified in bone matrix and termed bone sialoprotein 1, is secreted by a wide variety of cell types including osteoblasts and osteoclasts and has the potential to serve as a bridge between cells and hydroxyapatite crystals through RGD and polyaspartic acid motifs (Oldberg et al., *Proc. Natl. Acad. Sci. USA* 83: 8819-8823, 1986). Despite the broad range of potential functions for OPN, ablation of the OPN gene in mice has not revealed an obvious phenotype that can be clearly connected to a specific function (Liaw et al., *J. Clin. Invest.* 101: 1468-1478, 1998; Rittling et al., *J. Bone Min. Res.* 13: 1101-1111, 1998). Opn KO mice demonstrate subtle changes in bone mineralization, such as greater hydroxyapatite crystal size and crystallinity (Boskey et al., *Calcif. Tissue Int.* 71: 145-154, 2002).

SUMMARY OF THE INVENTION

MVs derived from primary osteoblasts from TNAP-/- hypophosphatasia mice have increased levels of PPi, a potent inhibitor of mineralization. PPi is produced in part by NTP-PPH activity and degraded in part by TNAP. PPi is also secreted into the matrix from the cell interior in a manner dependent on the presumed action of ANK as an anion channel. Transfection of TNAP cDNA into osteoblastic cell lines increases the level of NTPPPH activity in MVs while the reduction in TNAP levels in TNAP knock-out osteoblast-derived MVs is followed by a reduction in the levels of MVs' NTPPPH activity. The key function of TNAP in bone is degradation of PPi to remove this mineralization inhibitor and provide free phosphate for apatite deposition. PC-1 is a direct antagonist of TNAP function. ANK also antagonizes TNAP-dependent matrix calcification. Specifically, the activity of PC-1 inhibits initial MV apatite deposition at the level of MVs, but ANK inhibits propagation of apatite outside the MVs. Furthermore, loss of function of the two distinct skeletal TNAP antagonists, PC-1 and ANK, ameliorates TNAP deficiency-associated osteomalacia in vivo (Hessle et al., *Proc. Natl. Acad. Sci. USA* 99: 9445-9449, 2002). Conversely, the hyperossification associated with both PC-1 null mice and ANK-deficient (ank/ank) mice is ameliorated by deficiency of TNAP in vivo In hypophosphatasia the $PP_i$ pool increases due to lack of TNAP's inorganic pyrophosphatase activity. This, in turn, leads to an increase in OPN levels. The combined inhibitory effect of $PP_i$ and OPN on hydroxyapatite deposition results in rickets/osteomalacia. In NPP1 deficiency, the extracellular $PP_i$ and OPN pool decreases due to reduced production of $PP_i$ and hypermineralization takes place as inhibition of hydroxyapatite deposition is relaxed. Similarly in an ANK-deficiency state, $PP_i$ accumulates inside the osteoblast but the extracellular pool is reduced leading to hypermineralization. The simultaneous deletion of the Akp2 and Enpp1 gene correct the levels of extracellular $PP_i$ and OPN and mineralization is normalized. In the case of a TNAP and ANK double deficiency it appears that deleting one functional allele of ANK is sufficient to achieve a correction.

Therefore, the invention provides methods for altering matrix mineralization in a patient (human or a non-human animal), either systemically or locally, in a tissue (e.g., bone, cartilage or ligament). Such methods comprise modulating (increasing or decreasing) expression or an activity of TNAP, PC-1, or ANK function (e.g., an enzymatic activity) in the tissue. Invention methods are useful for treating patients affected by diseases including, without limitation, arterial calcification, ankylosing spondylitis, hypophosphatasia, ossification of the posterior longitudinal ligament, myositis ossificans, diffuse idiopathic skeletal hyperostosis, calcific tendonitis, rotator cuff disease of the shoulders, osteomalacia, metabolic bone disease associated with renal failure, bone spurs, cartilage or ligament degeneration due to hydroxyapatite crystal deposition, chondrocalcinosis, and osteoporosis.

According to one embodiment of the invention, a composition is administered to a patient comprising an effective amount of a substance that inhibits or reduces TNAP activity, whether by reducing TNAP expression (either transcriptionally or post-transcriptionally) or inhibiting TNAP enzyme activity. For example, TNAP activity can be inhibited by administering a composition comprising an effective amount of a TNAP inhibitor such as a well-known small molecule inhibitor (e.g., Tetramisole, levamisole, dexamisole, L-homoarginine, teophyllin or forphenicine) an antisense, siRNA or an antibody specific for TNAP. TNAP inhibitors are therefore useful for inhibiting or reducing matrix mineralization which, in turn, is useful in reducing symptoms of hyper-mineralization diseases such as ankylosing spondylitis, diffuse idiopathic skeletal hyperostosis, ossification of the posterior longitudinal ligament, bone spurs, arterial calcification, and degeneration of cartilage or ligament due to hydroxyapatite crystal deposition. According to a related aspect of the invention, compositions are provided that comprise an amount of a TNAP inhibitor that is effective in reducing matrix mineralization in a tissue of a patient.

In another embodiment of the invention, methods are provided for treating a patient affected by a PC-1 or an ANK deficiency comprising administering to the patient a composition comprising an amount of a TNAP inhibitor (e.g., from Tetramisole, levamisole, dexamisole, L-homoarginine, teophyllin, forphenicine, a TNAP antisense, siRNA or antibody) that is effective in reducing one or more symptoms associated with the PC-1 or an ANK deficiency. Methods are provided for treating a patient having a disease selected from arterial calcification, ankylosing spondylitis, ossification of the posterior longitudinal ligament, myositis ossificans, diffuse idiopathic skeletal hyperostosis, calcific tendonitis, rotator cuff disease of the shoulders, osteomalacia, metabolic bone disease associated with renal failure, bone spurs, cartilage or ligament degeneration due to hydroxyapatite crystal deposition, chondrocalcinosis, or osteoporosis, caused at least in part by deficient PC-1 or ANK activity or expression, comprising administering a compound that reduces expression or an activity of TNAP in a tissue of the patient affected by the disease.

According to another aspect of the invention, methods of treating a patient affected by hypophosphatasia are provided that comprise inhibiting or reducing expression or enzymatic activity of PC-1, ANK, or OPN in a tissue affected by hypophosphatasia. In one embodiment, a composition is administered to the patient that comprises an amount of a PC-1 inhibitor (e.g., PPADS, RB2, DIDS or suramin) that is effective in reducing one or more symptoms of hypophosphatasia. In another embodiment, a composition is administered to the patient that comprises an amount of an ANK inhibitor (e.g., probenecid) that is effective in reducing one or more symptoms of hypophosphatasia. In yet another embodiment, a composition is administered to the patient that comprises an amount of an OPN inhibitor that is effective in reducing one or more symptoms of hypophosphatasia. Such methods are useful for increasing or stimulating matrix mineralization which, in turn, is useful in reducing one or more symptoms of hypo-mineralization diseases such as hypophosphatasia, osteomalacia, metabolic bone disease associated with renal failure, and osteoporosis. According to another aspect of the invention, methods of treating a patient affected by a TNAP deficiency are provided comprising administering to the patient a composition comprising an amount of a PC-1 or ANK inhibitor that is effective in reducing one or more symptoms associated with the TNAP deficiency (e.g., hypophosphatasia, osteomalacia, metabolic bone disease associated with renal failure, or osteoporosis).

According to another aspect of the invention, methods of treating a patient affected with hyperphosphatasia comprising administering a compound that increases expression or an activity of OPN in a tissue of the patient affected by the hyperphosphatasia.

According to another aspect of the invention, methods of identifying a compound useful in treating a disorder associated with insufficient or deficient PC-1 or ANK activity or expression and methods of identifying a compound useful in treating a disorder associated with insufficient or deficient TNAP activity or expression are provided. In one embodiment, a method includes: providing an animal having deficient PC-1 or ANK activity or expression (e.g., a transgenic animal having mutated or a knockout of a PC-1 or ANK encoding gene, such as murine Enpp1 or ank/ank), wherein the animal has excessive mineralization in one or more tissues; administering a test compound that inhibits TNAP expression or an activity to the animal; and determining if the animal exhibits an improvement in a tissue that has excessive mineralization, wherein an improvement in the tissue identifies the test compound as a compound useful in treating a disorder associated with insufficient or deficient PC-1 or ANK activity or expression. In various particular aspects, the disorder is selected from arterial calcification, ankylosing spondylitis, ossification of the posterior longitudinal ligament, myositis ossificans, diffuse idiopathic skeletal hyperostosis, calcific tendonitis, rotator cuff disease of the shoulders, osteomalacia, metabolic bone disease associated with renal failure, bone spurs, cartilage or ligament degeneration due to hydroxyapatite crystal deposition, chondrocalcinosis, and osteoporosis. In another embodiment, a method includes: providing an animal having deficient TNAP activity or expression (e.g., a transgenic animal having a knockout or an animal having a naturally occurring mutation of a TNAP encoding gene such as murine Akp2), wherein the animal has deficient mineralization in one or more tissues; administering a test compound that inhibits PC-1 or ANK expression or activity to the animal; and determining if the animal exhibits an improvement in a tissue that has deficient mineralization, wherein an improvement in the tissue identifies the test compound as a compound useful in treating a disorder associated with insufficient or deficient TNAP activity or expression. In a particular aspect, the disorder comprises hypophosphatasia.

According to another aspect of the invention, methods of identifying patients having or at risk of having hypophosphatasia or a disorder associated with hypophosphatasia are provided. In one embodiment, a method includes providing a patient or a sample from a patient; and assaying the patient or sample from the patient or the sample for the amount of OPN; an amount of OPN greater than normal indicates the presence of hypophosphatasia or an increased risk of hypophosphatasia. Disorders include arterial calcification, ankylosing spondylitis, ossification of the posterior longitudinal ligament, myositis ossificans, diffuse idiopathic skeletal hyperostosis, calcific tendonitis, rotator cuff disease of the shoulders, osteomalacia, metabolic bone disease associated with renal failure, bone spurs, cartilage or ligament degeneration due to hydroxyapatite crystal deposition, chondrocalcinosis and osteoporosis.

According to another aspect of the invention, methods of identifying patients in need of treatment for hypophosphatasia or a disorder associated with hypophosphatasia are provided. In one embodiment, a method includes providing a patient or a sample from a patient; and assaying the patient or sample from the patient or the sample for the amount of OPN. An amount of OPN greater than normal indicates the presence of hypophosphatasia or an increased risk of hypophosphatasia, e.g., increased serum OPN in the range of 15-50 pg/ml.

According to another aspect of the invention, methods of identifying patients having or at risk of having hyperphosphatasia or a disorder associated with hyperphosphatasia are provided. In one embodiment, a method includes providing a patient or a sample from a patient, and assaying the patient or sample from the patient or the sample for the amount of OPN.

An amount of OPN less than normal indicates the presence of hyperphosphatasia or an increased risk of hyperphosphatasia.

According to another aspect of the invention, methods of identifying patients in need of treatment for hyperphosphatasia or a disorder associated with hyperphosphatasia are provided. In one embodiment, a method includes providing a patient or a sample from a patient, and assaying the patient or sample from the patient or the sample for the amount of OPN. An amount of OPN less than normal indicates the presence of hyperphosphatasia or an increased risk of hyperphosphatasia.

According to another aspect of the invention, methods of monitoring a patient receiving a treatment that inhibits PC-1 or ANK expression or activity are provided. In one embodiment, a method includes providing a patient or a sample from a patient, and assaying the patient or sample from the patient or the sample for the amount of OPN. A decreased amount of OPN after treatment indicates that the treatment has inhibited PC-1 or ANK.

According to another aspect of the invention, methods of monitoring a patient receiving a treatment that increases PC-1 or ANK expression or activity are provided. In one embodiment, a method includes providing a patient or a sample from a patient, and assaying the patient or sample from the patient or the sample for the amount of OPN. An increased amount of OPN after treatment indicates that the treatment increases PC-1 or ANK, e.g. increased serum OPN in the range of 15-150 pg/ml.

According to another aspect of the invention, methods of identifying compounds that modulate PC-1, ANK or TNAP expression or activity are provided. In one embodiment, a method includes administering a test compound to a cell or animal, and determining if the cell or animal exhibits an increase or a decrease in OPN expression or activity. An increase or decrease in OPN expression or activity identifies the test compound as a compound that modulates PC-1, ANK or TNAP expression or activity.

According to another aspect of the invention, methods of identifying candidate compounds for treating hypermineralization or hypomineralization are provided. In one embodiment, a method includes administering a test compound to a cell or animal, and determining if the cell or animal exhibits an increase or a decrease in OPN expression or activity. An increase or decrease in OPN expression or activity identifies the test compound as a candidate compound for treating hypermineralization or hypomineralization.

According to another aspect of the invention, methods of monitoring a patient receiving a treatment that modulates TNAP expression or activity are provided. In one embodiment, a method includes providing a patient or a sample from a patient, and assaying the patient or sample from the patient or the sample for the amount of OPN. An increased or decreased amount of OPN after treatment indicates that the treatment modulates TNAP expression or activity.

According to another aspect of the invention, kits are provided. In one embodiment, a kit includes an amount of a TNAP inhibitor (e.g., Tetramisole, levamisole, dexamisole, L-homoarginine, teophyllin, forphenicine, and a TNAP antisense, siRNA or antibody) effective to reduce matrix mineralization in a tissue of a patient having deficient PC-1 or ANK activity or expression, and instructions for administering said inhibitor to said patient on a label or packaging insert. In another embodiment, a kit includes an amount of a PC-1 inhibitor (e.g., PPADS, RB2, DIDS and suramin or a PC-1 antisense, siRNA or antibody) effective to increase matrix mineralization in a tissue of a patient having deficient TNAP activity or expression, and instructions for administering said inhibitor to said patient on a label or packaging insert. In yet another embodiment, a kit includes an amount of an ANK inhibitor (e.g., probenecid or an ANK antisense, siRNA or antibody) effective to increase matrix mineralization in a tissue of a patient having deficient TNAP activity or expression, and instructions for administering said inhibitor to said patient on a label or packaging insert.

BRIEF DESCRIPTION OF THE DRAWINGS

FIG. 1 shows a scheme for cross-breeding of the TNAP× PC-1 deficient mice. T: wild-type TNAP allele; t: null TNAP allele; P: wild-type PC-1 allele; p: null PC-1 allele.

FIG. 2 shows a scheme for cross-breeding of the TNAP× ANK deficient mice. T: wild-type TNAP allele; t: null TNAP allele; A: wild-type ank allele; a: mutant ank allele.

DETAILED DESCRIPTION OF THE INVENTION

Figure 3:
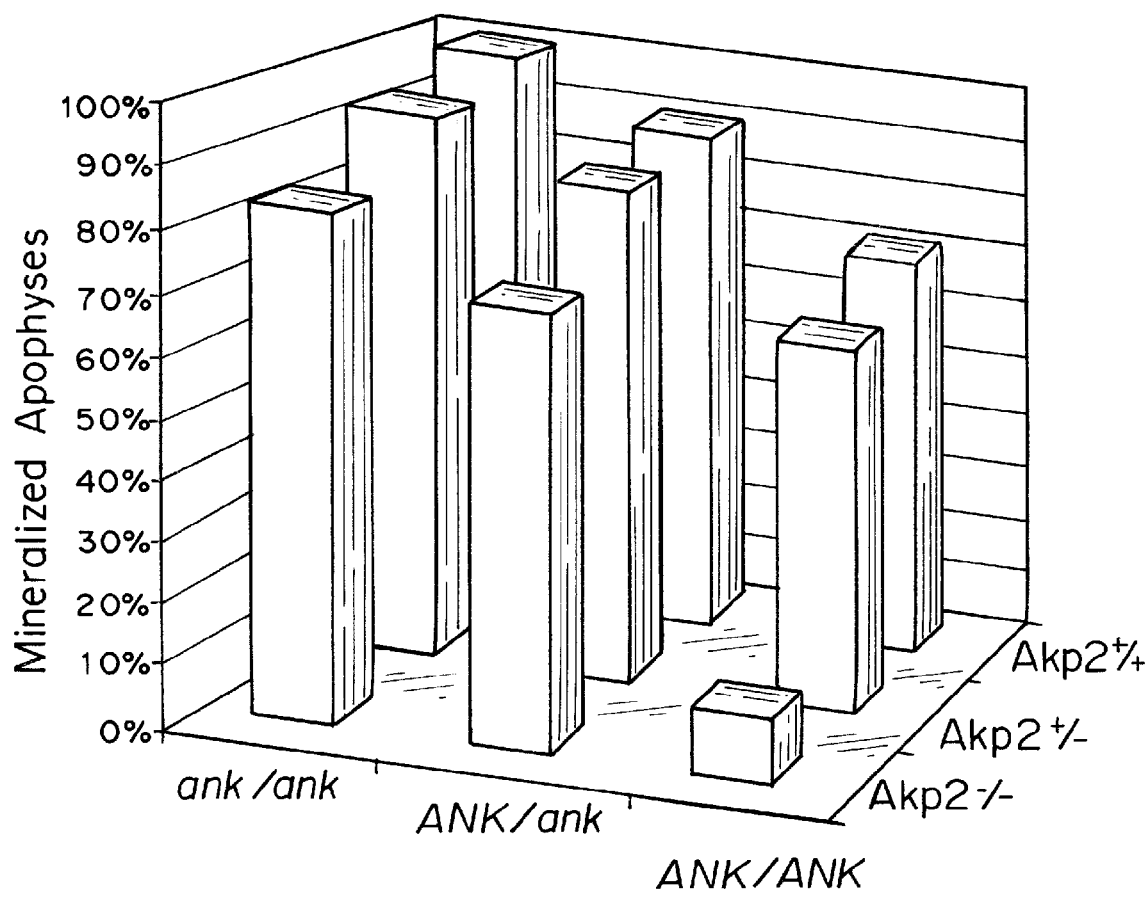
FIG. 3 shows the contribution of each Akp2 and ANK allele to the mineralization status of the lumbar spine. The percentage of mineralized apophyses is plotted as a function of the Akp2 and ANK genotypes.

PC-1-deficient mice and ank/ank mice serve as models of certain enthesopathies, including ossification of the posterior longitudinal ligament, diffuse idiopathic skeletal hyperostosis, and ankylosing spondylitis (Sali et al., In: *Conference Proceedings: Second International Symposium on Ecto-ATPases and Related Ectonucleotidases*; ed. Vanduffel and Lemmens, Shaker Publishing BV, Maastricht, Netherlands, pp. 267-282, 1999; Okawa et al., *Nature Gen*. 19:271-273, 1998; Krug et al., *J. Rheumatol*. 27:1257-1259, 2000). Terkeltaub and colleagues previously determined that IL-1 and TNFα inhibit PC-1 expression (Lotz et al., *Proc. Natl. Acad. Sci. USA* 92:10364-10368, 1995). Thus, locally deficient PC-1 expression (and possibly deficient ANK expression) are permissive for ossification of perispinal ligaments in enthesopathies and calcification at peripheral areas of periostitis. TNAP and other alkaline phosphatase isozymes are clinically and therapeutically useful for antagonizing the effects of dysregulated PC-1 and ANK function during ligamentous ossification in enthesopathies.

TNAP's key function in bone is degradation of PPi to remove this mineralization inhibitor. PC-1 is a direct antagonist of TNAP function. Also, ANK antagonizes TNAP and does so through a mechanism partly distinct from PC-1 action. These functions are demonstrated by downregulating the antagonists of TNAP in vivo by cross-breeding experiments and assessing the degree of phenotype rescue obtained when crossing TNAP and PC-1 deficient mice and TNAP and ank/ank deficient mice respectively. PPi plays a central regulatory role in controlling the expression levels of the enzymes that control PPi production, degradation and secretion, namely PC-1, TNAP and ANK.

The invention provides methods for modulating matrix mineralization in a tissue of a patient. In one embodiment, a composition is administered to modulate expression or an activity of TNAP in the tissue. In one aspect, the patient exhibits insufficient or deficient PC-1 expression or an activity. In another aspect, the patient is affected by hyper-mineralization, i.e., undesirable or excessive matrix mineralization. In yet another aspect, the patient is affected by a disease selected from arterial calcification, ankylosing spondylitis, ossification of the posterior longitudinal ligament, myositis ossificans, diffuse idiopathic skeletal hyperostosis, calcific tendonitis, rotator cuff disease of the shoulders, osteomalacia, metabolic bone disease associated with renal failure, bone spurs, cartilage or ligament degeneration due to hydroxyapatite crystal deposition, chondrocalcinosis, or osteoporosis. In another embodiment, a composition is administered to modulate expression or an activity of PC-1 or ANK in the tissue alone, or in combination. In one aspect, the patient exhibits insufficient or deficient TNAP expression or an activity. In another aspect, the patient is affected by hypo-mineralization, i.e., insufficient or deficient mineralization (e.g., hypophosphatasia).

The invention also provides methods for increasing matrix mineralization in a tissue of a patient having insufficient or deficient TNAP activity or expression. In one embodiment, a method includes administering an amount of a PC-1 or ANK inhibitor to the tissue or patient effective to inhibit PC-1 or ANK expression or activity. In one aspect, the tissue comprises bone, cartilage or ligament. In another aspect, the tissue exhibits insufficient or deficient matrix mineralization (e.g., hypophosphatasia).

The invention additionally provides methods of treating a patient having hypophosphatasia. In one embodiment, a method includes administering a compound that reduces or inhibits expression or an activity of PC-1, ANK, or OPN in a tissue of the patient affected by the hypophosphatasia. In one aspect, the amount of a PC-1, ANK or OPN inhibitor is effective to reduce or prevent one or more symptoms of the hypophosphatasia. In another aspect, a combination of compounds that reduces expression or an activity of PC-1, ANK or OPN is administered.

The invention further provides methods of treating a patient having a disease selected from arterial calcification, ankylosing spondylitis, ossification of the posterior longitudinal ligament, myositis ossificans, diffuse idiopathic skeletal hyperostosis, calcific tendonitis, rotator cuff disease of the shoulders, osteomalacia, metabolic bone disease associated with renal failure, bone spurs, cartilage or ligament degeneration due to hydroxyapatite crystal deposition, chondrocalcinosis, or osteoporosis, caused at least in part by insufficient or deficient PC-1 or ANK activity of expression. In one embodiment, a method includes administering a compound that reduces expression or an activity of TNAP in a tissue of the patient affected by the disease. In one aspect, the amount of a TNAP inhibitor is effective to reduce or prevent one or more symptoms of the disease.

Methods of the invention can be employed to treat a mineralization associated disorder. The invention therefore also provides methods of treating disorders associated with mineralization. As used herein, the term "mineralization associated disorder" means any undesirable physiological condition or pathological disorder in which modulating mineralization (e.g., increasing, stimulating, promoting, decreasing, reducing, inhibiting, preventing or stabilizing the mineralization status) leads to an improvement or a reduction of one or more undesirable symptoms of the condition or disorder. Physiological conditions or disorders in which mineralization participates include those that respond to modulating TNAP or PC-1 or ANK expression or activity.

Exemplary inhibitors useful in the invention include, for TNAP, Tetramisole, levamisole, dexamisole, L-homoarginine, teophyllin, forphenicine and TNAP antisense, TNAP siRNA and antibodies that bind TNAP. Exemplary inhibitors useful in the invention include, for PC-1, PPADS, RB2, DIDS and suramin, PC-1 antisense, PC-1 siRNA and antibodies that bind PC-1. Exemplary inhibitors for ANK include probenecid, ANK antisense, ANK siRNA and antibodies that bind ANK. Exemplary inhibitors for OPN include OPN antisense, OPN siRNA and antibodies that bind OPN.

Inhibitors further include Tetramisole, levamisole, dexamisole, L-homoarginine, teophyllin, forphenicine analogues, as well as PPADS, RB 2, DIDS, suramin and probenecid analogues. The term "analogue" means a structurally similar molecule that has at least part of the function of the comparison molecule. In other words, the analogue would still retain at least a part of the activity of the comparison molecule, i.e. a Tetramisole analogue would retain at least a part of the TNAP inhibitory activity of Tetramisole.

Inhibitors further include derivatives of Tetramisole, levamisole, dexamisole, L-homoarginine, teophyllin, forphenicine, PPADS, RB2, DIDS, suramin and probenecid. As used herein, the term "derivative" means a modified form of the molecule, that is, the molecule is chemically or otherwise modified in comparison to the original form. Again, the derivative would still retain at least a part of the activity of the unmodified molecule. For example, a derivative of a TNAP inhibitor would be a modified form of an antagonist molecule that inhibits, decreases, reduces or prevents TNAP expression or an activity. Thus, TNAP, PC-1 and ANK inhibitors include derivatives of Tetramisole, levamisole, dexamisole, L-homoarginine, teophyllin, forphenicine, PPADS, RB2, DIDS, suramin and probenecid.

Additional inhibitors of TNAP, PC-1, ANK or OPN expression or an activity (e.g., other small molecules and dominant negative inhibitors), including analogues and derivatives can be identified using TNAP, PC-1, ANK or OPN expression or activity assays set forth herein or known in the art (see, for example, Examples 1, 8, 9 and 15; Register et al., *J. Biol. Chem.* 259:922 (1984); Fallon et al., *Laboratory Investigation* 43:489 (1980); and Grobben et al., *Brit. J. Pharamacol.* 130:139(2000)), histological assays of osteoblasts or morphological assays of osteoblast containing tissues (see, for example, Examples 1, 5, 6, 11, 13 and 17) or molecular modeling. TNAP, PC-1, ANK or OPN may be detected using antibodies, for example, commercially available TNAP detection kits; Tandem-R Ostase (Beckman Coulter, Inc., San Diego, Calif.) and Alkphase-B (Quidel Corp., San Diego, Calif.).

Inhibitors also include TNAP, PC-1, ANK and OPN antisense. As used herein, the term "antisense" refers to a polynucleotide or peptide nucleic acid capable of binding to a specific DNA or RNA sequence. Such antisense can inhibit TNAP, PC-1, ANK or OPN expression which, in turn decreases or increases mineralization, respectively. Such antisense can be made by producing a polynucleotide targeted to all or a region of TNAP, PC-1, ANK or OPN gene (e.g., 5' or 3' untranslated region, intron or gene coding region) and testing for inhibition of TNAP, PC-1, ANK or OPN gene expression, for example, in a cell that expresses TNAP, PC-1, ANK or OPN.

Antisense may be designed based on gene sequences available in the database. TNAP, in mouse designated Akp2, accession no. NM 007431 and GI 6671532; in human designated ALPL, accession no. NM 000478 and GI 13787192. PC-1, in mouse designated Enpp1, accession no. AF 339910 and GI 15099944; in human designated Enpp1, accession no. NM 006208 and GI 13324676 ANK, in mouse designated ANK, accession no. AF274752; in human designated ANKH, accession no. NM 019847 and NM 054027. OPN in mouse designated OPN, accession no. NM 009386 and GI 6678112, in human designated OPN or SPP-1, accession no. NM 000582 and GI 4759165.

Antisense includes single, double or triple stranded polynucleotides and peptide nucleic acids (PNAs) that bind RNA transcript or DNA. For example, a single stranded nucleic acid can target TNAP, PC-1, ANK or OPN transcript (e.g., mRNA). Oligonucleotides derived from the transcription initiation site of the gene, e.g., between positions −10 and +10 from the start site, are a particular one example. Triplex forming antisense can bind to double strand DNA thereby inhibiting transcription of the gene. The use of double stranded RNA sequences (known as "RNAi") for inhibiting gene expression is known in the art (see, e.g., Kennerdell et al., *Cell* 95:1017(1998); Fire et al., *Nature*, 391:806(1998)). Double stranded RNA sequences from a TNAP, PC-1, ANK or OPN coding region may therefore be used to inhibit expression.

Inhibitors further include TNAP, PC-1, ANK and OPN siRNA. The term "siRNA" refers to small interfering double-stranded RNA molecules for use in RNA interference methods. RNA interference (RNAi) is a process of sequence-specific gene silencing by post-transcriptional RNA degradation, which is initiated by double-stranded RNA (dsRNA) homologous to a sequence of the silenced gene. A particular example of a double-stranded RNA (dsRNA) contains sense and antisense strands of about 21 contiguous nucleotides corresponding to the target gene that hybridize with 19 RNA nucleotides, leaving overhangs of two nucleotides at each 3' end (Elbashir et al., *Nature* 411:494-498 (2001); Zamore, *Nat. Struct. Biol.* 8:746-750 (2001)). dsRNAs of about 25-30 nucleotides have also been used for RNAi (Karabinos et al., *Proc. Natl. Acad. Sci. USA* 98:7863-7868 (2001). dsRNA can be synthesized in vitro and introduced into a cell by methods known in the art. By such methods, translation of the target polypeptide can be decreased.

Antisense molecules are typically 100% complementary to the sense strand but may be "partially" complementary in which only some of the nucleotides bind to the sense molecule (less than 100% complementary, e.g., 95%, 90%, 80%, 70% and sometimes less). Antisense molecules include and may be produced by methods including transcription from a gene or chemically synthesized (e.g., solid phase phosphoramidite synthesis).

Ribozymes, enzymatic RNA molecules, may also be used to catalyze the specific cleavage of RNA thereby inhibiting expression of the corresponding protein. The mechanism of ribozyme action involves sequence-specific hybridization of the ribozyme molecule to complementary target RNA, followed by endonucleolytic cleavage. Specific examples include engineered hammerhead motif ribozyme molecules that can specifically and efficiently catalyze endonucleolytic cleavage of sequences encoding proteins such as TNAP, PC-1, ANK or OPN.

Specific ribozyme cleavage sites within any potential RNA target are initially identified by scanning the target molecule for cleavage sites which include the following sequences: GUA, GUU, and GUC. Once identified, RNA sequences of between about 15 and 20 ribonucleotides corresponding to the region of the target containing the cleavage site may be evaluated for secondary structural features which may render the oligonucleotide inoperable. The suitability of candidate targets sequences may also be evaluated by testing accessibility to hybridization with complementary oligonucleotides using ribonuclease protection assays.

Antisense polynucleotides may include L- or D-forms and additionally may be modified in order to provide resistance to degradation when administered to a patient. Particular examples include 5' and 3' linkages that are resistant to endonucleases and exonucleases present in various tissues or fluids in the body of an animal.

Antisense polynucleotides, to decrease expression of TNAP, PC-1, ANK or OPN do not require expression control elements to function in vivo. Such antisense molecules can be absorbed by the cell or enter the cell via passive diffusion. Antisense may also be introduced into a cell using a vector, such as a virus vector. However, antisense may be encoded by a nucleic acid so that it is transcribed, and, further, such a nucleic acid encoding an antisense may be operatively linked to an expression control element for sustained or increased expression of the encoded antisense in cells or in vivo.

The term "vector" refers to a plasmid, virus or other vehicle known in the art that can be manipulated by insertion or incorporation of a polynucleotide. Such vectors can be used for genetic manipulation (i.e., "cloning vectors") or can be used to transcribe or translate the inserted polynucleotide (i.e., "expression vectors"). A vector generally contains at least an origin of replication for propagation in a cell and a promoter. Control elements, including expression control elements as set forth herein, present within a vector are included to facilitate transcription and translation (e.g., splicing signal for introns, maintenance of the correct reading frame of the gene to permit in-frame translation of mRNA and, stop codons etc.).

The term "expression control element" refers to one or more nucleic acid sequence elements that regulate or influence expression of a nucleic acid sequence to which it is operatively linked. An expression control element operatively linked to a nucleic acid sequence controls transcription and, as appropriate, translation of the nucleic acid sequence. An expression control element can include, as appropriate, promoters, enhancers, transcription terminators, gene silencers, a start codon (e.g., ATG) in front of a protein-encoding gene, etc.

A "promoter" is a minimal sequence sufficient to direct transcription. Although generally located 5' of the coding sequence, they can be located in introns or 3' of the coding sequence. Both constitutive and inducible promoters are included in the invention (see e.g., Bitter et al., *Methods in Enzymology*, 153:516-544 (1987)). Inducible promoters are activated by external signals or agents. Repressible promoters are inactivated by external signals or agents. Derepressible promoters are normally inactive in the presence of an external signal but are activated by removal of the external signal or agent. Promoter elements sufficient to render gene expression controllable for specific cell-types, tissues or physiological conditions (e.g., heat shock, glucose starvation) are also included within the meaning of this term.

For mammalian cell expression, constitutive promoters such as SV40, RSV and the like or inducible or tissue specific promoters derived from the genome of mammalian cells (e.g., metallothionein promoter) or from mammalian viruses (e.g., the mouse mammary tumor virus long terminal repeat; the adenovirus late promoter) or osteoclasts (e.g., Cbfal, collagen I or osteolcalcin gene promoter) may be used. Promoters produced by recombinant DNA or synthetic techniques may also be used to provide for transcription of antisense. Mammalian expression systems that utilize recombinant viruses or viral elements to direct expression may be engineered, if desired. For example, when using adenovirus expression vectors, the sequence coding for antisense may be ligated to an adenovirus transcription/translation control complex, e.g., the late promoter and tripartite leader sequence. (see e.g., Mackett et al., *Proc. Natl. Acad. Sci. USA*, 79:7415(1982); Mackett et al., *J. Virol.*, 49:857(1984); and Panicali et al., *Proc. Natl. Acad. Sci. USA*, 79:4927(1982)).

Vectors based on bovine papilloma virus (BPV) have the ability to replicate as extrachromosomal elements (Sarver et al., *Mol. Cell. Biol.*, 1:486 (1981)). Shortly after entry of an extrachromosomal vector into mouse cells, the vector replicates to about 100 to 200 copies per cell. Because transcription does not require integration of the plasmid into the host's chromosome, a high level of expression occurs. Alternatively, the retroviral genome can be modified for use as a vector capable of introducing and directing the expression of the gene in host cells (Cone et al., *Proc. Natl. Acad. Sci. USA*, 81:6349(1984)).

These vectors can be used for stable expression by including a selectable marker in the plasmid. A number of selection systems may be used to identify or select for transformed host cells, including, but not limited to the herpes simplex virus thymidine kinase gene (Wigler et al., *Cell*, 11:223(1977)), hypoxanthine-guanine phosphoribosyltransferase gene (Szybalska et al., *Proc. Natl. Acad. Sci. USA*, 48:2026(1962)), and the adenine phosphoribosyltransferase (Lowy et al., *Cell*, 22:817(1980)) genes can be employed in tk-, hgprt- or aprt- cells respectively. Additionally, antimetabolite resistance can be used as the basis of selection for dhfr, which confers resistance to methotrexate (Wigler et al., *Proc. Natl. Acad. Sci. USA*, 77:3567 (1980); O'Hare et al., *Proc. Natl. Acad. Sci. USA*, 78:1527(1981)); the gpt gene, which confers resistance to mycophenolic acid (Mulligan et al., *Proc. Natl. Acad. Sci. USA*, 78:2072(1981); the neomycin gene, which confers resistance to the aminoglycoside G-418 (Colberre-Garapin et al., *J. Mol. Biol.*, 150:1(1981)); and the hygromycin gene, which confers resistance to hygromycin (Santerre et al., *Gene*, 30:147(1984)).

Mammalian expression systems further include vectors specifically designed for in vivo applications. Such systems include adenoviral vectors (U.S. Pat. Nos. 5,700,470 and 5,731,172), adeno-associated vectors (U.S. Pat. Nos. 5,354, 678, 5,604,090, 5,780,447), herpes simplex virus vectors (U.S. Pat. No. 5,501,979) and retroviral vectors (U.S. Pat. Nos. 5,624,820, 5,693,508 and 5,674,703 and WIPO publications WO92/05266 and WO92/14829). Bovine papilloma virus (BPV) has also been employed in gene therapy (U.S. Pat. No. 5,719,054). Such vectors also include CMV based vectors (U.S. Pat. No. 5,561,063). In addition to viral vectors suitable for expression in vivo, lipids for intracellular delivery of polypeptides (including antibodies) and polynucleotides (including antisense) also are contemplated (U.S. Pat. Nos. 5,459,127 and 5,827,703). Combinations of lipids and adeno-associated viral material also can be used for in vivo delivery (U.S. Pat. No. 5,834,441).

Inhibitors further include antibody that specifically binds TNAP, PC-1, ANK or OPN. Such antibodies can inhibit an activity of TNAP, PC-1, ANK or OPN which, in turn decreases or increases mineralization, respectively. Antibodies to TNAP are described, for example, in Bailyes et al. (*Biochem. J.* 244:725 (1987)); Hill and Wolfert (*Clin. Chim. Acta* 186:315 (1990); Panigrahi et al. (*Clin. Chem.* 40:822 (1994)); Gomez et al. (*Clin. Chem.* 41:1560 (1995)); and Broyles et al. (*Clin. Chem.* 44:2139 (1998)).

The term "antibody" includes intact IgG, IgD, IgA, IgM and IgE immunoglobulin molecule, two full length heavy chains linked by disulfide bonds to two full length light chains, as well as subsequences (i.e. fragments) of immunoglobulin molecules, for example, Fab, Fab', (Fab')$_2$, Fv, and single chain antibody, e.g., scFv, which are capable of binding to an epitopic determinant present in TNAP, PC-1, ANK or OPN. Antibodies may comprise full-length heavy and light chain variable domains, $V_H$ and $V_L$, individually or in any combination. Other antibody fragments are included so long as the fragment retains the ability to selectively bind TNAP, PC-1, ANK or OPN.

Polyclonal and monoclonal antibodies can be made using methods well known in the art. For example, intact polypeptide or peptide fragments of TNAP, PC-1, ANK or OPN polypeptide can be used as immunizing antigen to produce polyclonal antibodies. The polypeptide or peptide used to immunize an animal may be derived from translated DNA or chemically synthesized and conjugated to a carrier protein, if desired. Such commonly used carriers which are chemically coupled to the immunizing peptide include, for example, keyhole limpet hemocyanin (KLH), thyroglobulin, bovine serum albumin (BSA), and tetanus toxoid.

Monoclonal antibodies are made by methods well known to those skilled in the art (Kohler et al., *Nature*, 256:495 (1975); and Harlow et al., "Antibodies: A Laboratory Manual," Cold Spring Harbor Pub. (1988)). Briefly, monoclonal antibodies can be obtained by injecting mice with antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques which include, for example, affinity chromatography with Protein-A Sepharose, size-exclusion chromatography, and ion-exchange chromatography (see e.g., Coligan et al., *Current Protocols in Immunology* sections 2.7.1-2.7.12 and sections 2.9.1-2.9.3; and Barnes et al., "Methods in Molecular Biology," 10:79-104, Humana Press (1992)).

Antibodies also include humanized and fully human antibodies. A "humanized" monoclonal antibody may be produced by transferring non-human complementarity determining regions (CDR) from heavy and light variable chains of the donor immunoglobulin into a human variable domain acceptor, and then substituting human amino acids in the framework regions for the non-human counterparts. Any mouse, rat, guinea pig, goat, non-human primate (e.g., ape, chimpanzee, macaque, orangutan, etc.) or other animal antibody may be used as a CDR donor for producing humanized antibody. Murine antibodies secreted by hybridoma cell lines can also be used. Donor CDRs are selected based upon the antigen to which the antibody binds. Thus, donor CDRs include sequences from antibodies that bind to The use of antibody components derived from humanized monoclonal antibodies obviates potential problems associated with the immunogenicity of murine constant regions. Techniques for producing humanized monoclonal antibodies are described, for example, by Jones et al., *Nature*, 321:522 (1986); Riechmann et al., *Nature*, 332:323 (1988); Verhoeyen et al., *Science*, 239:1534 (1988); Carter et al., *Proc. Natl. Acad. Sci. USA*, 89:4285 (1992); Sandhu, *Crit. Rev. Biotech.*, 12:437 (1992); and Singer et al., *J. Immunol.*, 150:2844 (1993).

"Human" monoclonal antibodies can be obtained from transgenic mice that have been "engineered" to produce specific human antibodies in response to antigenic challenge. In this technique, elements of the human heavy and light chain loci have been introduced into strains of mice derived from embryonic stem cell lines that contain targeted disruptions of the endogenous heavy and light chain loci. The transgenic mice can synthesize human antibodies that bind to human antigens, and can be used to produce human antibody-secreting hybridomas. Methods for obtaining human antibodies from such transgenic mice are described by Green et al., *Nature Genet.*, 7:13 (1994); Lonberg et al., *Nature*, 368:856 (1994); and Taylor et al., *Int. Immunol.*, 6:579 (1994).

Antibody subsequences (e.g., Fab, Fab', (Fab')$_2$, Fv, and single chain antibody (SCA), e.g., scFv fragments) can be prepared by genetic engineering of nucleic acid encoding the portion of the antibody or the chimera, proteolytic hydrolysis of the intact antibody. Single-chain antigen binding proteins (scFv) are prepared by constructing a structural gene comprising nucleic acid sequences encoding the $V_H$ and $V_L$ domains connected by an oligonucleotide. The structural gene is inserted into an expression vector, which is subsequently introduced into a host cell. The recombinant host cells synthesize a single polypeptide chain with a linker peptide bridging the two V domains. Methods for producing sFvs are described, for example, by Whitlow et al., *Methods: A Companion to Methods in Enzymology* 2:97 (1991); Bird et al., *Science* 242:423 (1988); U.S. Pat. No. 4,946,778; and Pack et al., *Bio/Technology* 11:1271 (1993)).

Pepsin or papain digestion of whole antibodies can be used to generate antibody fragments. In particular, an Fab fragment consists of a monovalent antigen-binding fragment of an antibody molecule, and can be produced by digestion of a whole antibody molecule with the enzyme papain, to yield a fragment consisting of an intact light chain and a portion of a heavy chain. An (Fab')$_2$ fragment of an antibody can be obtained by treating a whole antibody molecule with the enzyme pepsin, without subsequent reduction. An Fab' fragment of an antibody molecule can be obtained from (Fab')$_2$ by reduction with a thiol reducing agent, which yields a molecule consisting of an intact light chain and a portion of a heavy chain. Two Fab' fragments are obtained per antibody molecule treated in this manner.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. The association may be non-covalent or may be covalent, such as a chemical cross-linking agent or an intermolecular disulfide bond (Inbar et al., *Proc. Natl. Acad Sci. USA* 69:2659(1972); Sandhu *Crit. Rev. Biotech.* 12:437 (1992)). For example, Fv fragments can comprise $V_H$ and $V_L$ chains connected by a peptide linker.

Inhibitors additionally include dominant negative forms of TNAP, PC-1, ANK or OPN. Such dominant negative forms may inhibit interaction of the native endogenous protein with a component of the signaling pathway thereby inhibiting the native endogenous protein in participating in the signaling pathway. For example, a TNAP, PC-1, ANK or OPN protein that lacks enzymatic activity or ligand binding activity can exert dominant negative activity if it sequesters the substrate or receptor from native endogenous TNAP, PC-1, ANK or OPN protein thereby inhibiting endogenous TNAP, PC-1, ANK or OPN protein function.

The term "effective" when used in reference to "amount" means the quantity sufficient to produce the desired effect, or a "therapeutic effect." Thus, for example, an "effective amount" will be sufficient to increase, stimulate, promote, or inhibit, reduce, decrease, or prevent mineralization or demineralization, or any of the biological or pathophysiological features that characterize hypo- or hyper-mineralization as described herein or known in the art. Doses sufficient to provide an "effective amount" for treating, ameliorating or improving a biological or pathophysiological feature that characterizes hypo- or hyper-mineralization (e.g., undesirable, aberrant or abnormal mineralization or demineralization) will therefore be sufficient to reverse, ameliorate or improve one or more of the characteristics or symptoms of the condition or reduce the severity of the condition. Inhibiting, delaying or preventing a progression or worsening of the condition is also considered a satisfactory outcome. Amounts of tertamisole, a mixture of levanisole and dexamisole, will be from about 5 to 20, more likely 10 to 15 μg/gm body weight. Amounts for increasing OPN typically achieve 15-150 picograms/ml plasma OPN.

An amount is also considered effective when the dosage frequency or amount that the patient was administered to treat a disorder is reduced in comparison to the dosage frequency or amount administered prior to administering a TNAP, PC-1, ANK or OPN inhibitor. Contacting a sufficient number of target cells in an affected tissue of the subject with a TNAP, PC-1, ANK or OPN inhibitor can improve any one of these parameters thereby altering the course of the pathology.

The concentration of a composition required to be effective will depend on the organism targeted, the general health, age, sex or race of the subject, the disorder being treated, the extent or severity of the disorder, the clinical endpoint desired (e.g., increased or decreased mineralization, or inhibiting further changes in mineralization status), the formulation of the composition. The skilled artisan will appreciate the factors that may influence the dosage and timing required to provide an effective amount (see for example, Ansel et al., "Pharmaceutical Drug Delivery Systems," 5th ed. (Lea and Febiger (1990), Gennaro ed.). Doses can also be determined empirically or determined using animal disease models (e.g., using the TNAP and PC-1 transgenic knockout animals, mice carrying the ank/ank mutation, etc.) or optionally in human clinical trials. Prophylactic and other treatments may be specifically tailored or modified based on pharmacogenomic data.

The invention methods can be supplemented with other compositions and used in conjunction with other patient treatment protocols. The invention methods can be performed prior to, contemporaneously with or following treatment with another therapeutic protocol. Such drugs and therapeutic protocols include, for example, in vivo or ex vivo gene therapy, in which TNAP, PC-1, ANK or OPN function is replaced by TNAP, PC-1, ANK or OPN, or another gene that provides at least a part of the missing activity (e.g., for TNAP, an alkaline phosphatase encoding gene) by using appropriate vectors to introduce the gene into osteoprogenitor bone marrow stem cells. An alternative therapy is to transplant syngenic normal osteoprogenitor bone marrow cells into a recipient patient lacking expression or an activity of TNAP, PC-1, ANK or OPN.

The term "patient" refers to animals, typically mammalian animals, such as a non human primate (apes, gibbons, chimpanzees, orangutans, macaques), a domestic animal (dogs and cats), a farm animal (horses, cows, goats, sheep, pigs), experimental animal (mouse, rat, rabbit, guinea pig) and humans having or at risk of having insufficient or deficient TNAP, PC-1, ANK or OPN expression or an activity or hypo- or hypermineralization. Subjects include hypo- or hypermineralization model animals (e.g., mice) as set forth herein and known in the art (see, for example, Waymire et al., Nature Genet. 11:45 (1995); Okawa et al., Nature Genet 19:271 (1998) and Ho et al., Science 289:265 (2000)).

Target patients therefore include subjects having insufficient or deficient TNAP, PC-1 or ANK expression or activity, or that exhibit hypo- or hypermineralization in one or more tissues. Target subjects may not exhibit overt symptoms of hypo- or hypermineralization but may nevertheless be identified by assaying for deficient TNAP, PC-1 or ANK expression or an activity. For example, many hypophosphatasia patients do not have the lethal form of the disease but instead are afflicted with the adult or odontohypophosphatasia forms. A simple blood analysis for TNAP activity can reveal a reduced level of TNAP activity and treatment can be initiated to inhibit or prevent the future development of spontaneous fractures and early loss of teeth associated with adult hypophosphatasia. Similarly, the presence of heterozygous conditions of TNAP, PC-1 or ANK can be detected; positively identified patients could be treated to prevent any progression of the disease at an early stage. Even individuals heterozygous for TNAP, PC-1 and ANK mutations display mild abnormalities. Accordingly, prophylactic treatment methods also are included and the term "patient" includes subjects at risk of hypo- or hyper-mineralization, such subjects genetically predisposed to a disease due to the absence of a functional gene (e.g., TNAP, PC-1 or ANK) or presence of an aberrantly or only partially functional gene (e.g., due to a genetic polymorphism, such subjects identified through routine genetic screening or by inquiring into the subjects' family history before significant clinical manifestations appear or increase in severity.

Pharmaceutical compositions include "pharmaceutically acceptable" and "physiologically acceptable" carriers, diluents or excipients. As used herein the term "pharmaceutically acceptable" and "physiologically acceptable" includes solvents (aqueous or non-aqueous), solutions, emulsions, dispersion media, coatings, isotonic and absorption promoting or delaying agents, compatible with pharmaceutical administration. Such formulations can be contained in a tablet (coated or uncoated), capsule (hard or soft), microbead, emulsion, powder, granule, crystal, suspension, syrup or elixir. Supplementary active compounds (e.g., preservatives, antibacterial, antiviral and antifungal agents) can also be incorporated into the compositions.

Pharmaceutical compositions can be formulated to be compatible with a particular route of administration. Thus, pharmaceutical compositions include carriers, diluents, or excipients suitable for administration by various routes.

Pharmaceutical compositions for parenteral, intradermal, or subcutaneous administration can include a sterile diluent, such as water, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Pharmaceutical compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. In many cases, isotonic agents, for example, sugars, polyalcohols such as manitol, sorbitol, sodium chloride are included in the composition.

Sterile injectable solutions can be prepared by incorporating the active compound in the required amount in an appropriate solvent with one or a combination of above ingredients followed by filtered sterilization. Generally, dispersions are prepared by incorporating the active compound into a sterile vehicle containing a basic dispersion medium and other ingredients from those above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. For transdermal administration, the active compounds are formulated into ointments, salves, gels, or creams as generally known in the art.

TNAP, PC-1, ANK and OPN inhibitors can be prepared with carriers that will protect them against rapid elimination from the body, such as a controlled release formulation or a time delay material such as glyceryl monostearate or glyceryl stearate. The compositions can also be delivered using implants and microencapsulated delivery systems.

Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to cells or tissues using antibodies or viral coat proteins) can also be used as pharmaceutically acceptable carriers. These can be prepared according to methods known to those skilled in the art, for example, as described in U.S. Pat. No. 4,522,811.

A pharmaceutical composition including a gene therapy vector can include the gene therapy vector in an acceptable excipient, diluent or carrier, or can comprise a slow release matrix in which the gene delivery vehicle is imbedded. Alternatively, where the gene delivery vector is produced intact from recombinant cells, e.g., retroviral vectors, the pharmaceutical composition can include one or more of the cells that produce the gene delivery vector.

Additional pharmaceutical formulations appropriate for administration are known in the art and are applicable to the invention (see, e.g., *Remington's Pharmaceutical Sciences* (1990) 18th ed., Mack Publishing Co., Easton, Pa.; *The Merck Index* (1996) 12th ed., Merck Publishing Group, Whitehouse, N.J.; and *Pharmaceutical Principles of Solid Dosage Forms*, Technonic Publishing Co., Inc., Lancaster, Pa., (1993)).

The pharmaceutical formulations can be packaged in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the pharmaceutical carrier or excipient.

Methods of administration include systemic and targeted administration. Particular examples of routes of administration include parenteral, e.g., intravenous, intrarterial, intacavity (e.g., within joints of the bones), intramuscular, intradermal, subcutaneous, intracranial, transdermal (topical), and transmucosal administration. Patients may be administered by infusion or injection, by a single bolus or by repeated doses.

Where cell or tissue targeting is desired the target tissue may be injected or infused or a delivery device positioned so as to deliver the composition to the targeted tissue. Targeting can also be achieved by using targeting molecules (e.g., proteins) that bind to a cell surface molecule (e.g., receptor or matrix protein) present on the cell or population of cell types (e.g., osteoblasts). For example, antibodies or antibody sub-sequences (e.g., Fab region) that bind to a cell surface protein can be included in the delivery systems in order to facilitate cell or tissue targeting. Viral coat proteins that bind particular cell surface proteins can be used to target cells or tissues for expression of the modified blood clotting factors of the invention. For example, naturally occurring or synthetic (e.g. recombinant) retroviral envelope proteins with known cell surface protein binding specificity can be employed in the retroviral vectors or liposomes containing nucleic acid anti-sense in order to intracytoplasmically deliver the molecule into target cells expressing the cell surface protein. Thus, delivery vehicles, including viral vectors and colloidal dispersion systems, can be made to have a protein or a proteinaceous coat in order to facilitate targeting or intracytoplasmic delivery and expression of a TNAP, PC-1, ANK or OPN antisense or antibody or other inhibitory molecule.

Appropriate tissue targets include any tissue that expresses TNAP,PC-1, ANK or OPN or that undergoes mineralization or may be affected by mineralization. Accordingly, any tissues that includes osteoblasts are an appropriate target. Particular non-limiting examples of target tissues include bone, cartilage and ligament. Additional examples include blood vessels (e.g., arteries such as carotid, pulmonary, coronary, etc.) as artherial calcification is associated with artheriosclerotic plaque formation.

The invention provides kits comprising invention compositions, including pharmaceutical formulations, packaged into suitable packaging material. In one embodiment, a kit includes an amount of a TNAP inhibitor effective to inhibit, reduce or prevent matrix mineralization in a tissue of a patient having deficient PC-1 or ANK activity or expression, and instructions for administering said inhibitor to said patient on a label or packaging insert. In one aspect, the inhibitor is selected from L-tetramisole, D-tetramisole, levamisole, dexamisole, L-homoarginine, teophyllin, forphenicine and a TNAP antisense or antibody. In another embodiment, a kit includes an amount of OPN effective to inhibit, reduce or prevent matrix mineralization in a tissue of a patient having deficient PC-1 or ANK activity or expression, and instructions for administering said inhibitor to said patient on a label or packaging insert. In another embodiment, a kit includes an amount of a PC-1 or ANK inhibitor effective to increase matrix mineralization in a tissue of a patient having deficient TNAP activity or expression, and instructions for administering said inhibitor to said patient on a label or packaging insert. In one aspect, the inhibitor is selected from PPADS, RB2, DIDS, suramin, or probenecid and a PC-1 or ANK antisense or antibody. In various aspects, the label or insert includes additional instructions appropriate for a particular tissue to be treated.

Kits further include an amount of a combination of PC-1 and ANK inhibitors effective to increase matrix mineralization in a tissue of a patient having deficient TNAP activity or expression, and instructions for administering said inhibitor to said patient on a label or packaging insert.

The invention also provides kits containing a transgenic animal of the invention, and instructions for screening test compounds to identify inhibitors of TNAP,PC-1, ANK or OPN on a label or packaging insert. In one aspect, the transgenic animal comprises a mouse that includes all or a part of TNAP, PC-1, ANK or OPN encoding gene knocked our or rendered non-functional by genetic means.

As used herein, the term "packaging material" refers to a physical structure housing the components of the kit. The packaging material can maintain the components sterilely, and can be made of material commonly used for such purposes (e.g., paper, corrugated fiber, glass, plastic, foil, etc.). The label or packaging insert can indicate that the kit is to be used in a method of the invention, for example.

Kits of the invention therefore can additionally include instructions for using the kit components in a method of the invention. Instructions can include instructions for practicing any of the methods of the invention described herein. Thus, the pharmaceutical compositions can be included in a container, pack, or dispenser together with instructions for administration. Instructions may additionally include indications of a satisfactory clinical endpoint or any adverse symptoms that may occur, or additional information required by the Food and Drug Administration for use on a human.

The instructions may be on "printed matter," e.g., on paper of cardboard within the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Invention kits can additionally include a buffering agent, a preservative, or a protein/nucleic acid stabilizing agent. The kit can also include components for detecting changes in mineralization status either directly (whole body bone density measurements) or indirectly (e.g., amounts of PPi or other molecule indicative of mineralization status), for example, to monitor treatment efficacy. Each component of the kit can be enclosed within an individual container and all of the various containers can be within a single package.

As used herein, the term "transgenic animal" refers to a non-human animal whose somatic or germ line cells bear genetic information received, directly or indirectly, by genetic manipulation at the subcellular level, such as by nucleic acid microinjection. In the present context, a "transgenic animal" also includes progeny animals produced by mating of such genetically manipulated transgenic animals. The term "transgenic" further includes cells or tissues (i.e., "transgenic cell," "transgenic tissue") obtained from a transgenic animal genetically manipulated as described herein. Transgenic animals can be either heterozygous or homozygous with respect to the transgene, although it is likely that germline transgenics will be used. Methods for producing transgenic animals, including mice, sheep, pigs and frogs, are well known in the art (see, e.g., U.S. Pat. Nos. 5,721,367, 5,695,977, 5,650,298, and 5,614,396) and, as such, are additionally included.

The term "transgenic" also includes any animal whose genome has been altered by in vitro manipulation of the early embryo or fertilized egg or by transgenic technology to induce a gene knockout. The term "gene knockout" as used herein, refers to the disruption of all or a part of a targeted gene in vivo with a loss of function that has occurred naturally, e.g., by a spontaneous mutation, or by any transgenic technology which can produce an animal in which an endogenous gene has been rendered non-functional or "knocked out."

Thus, in accordance with the invention, there are provided non-human transgenic animals produced by transgenic technology having absent or decreased TNAP, PC-1 and ANK expression or activity, and animals having absent or decreased combinations of TNAP, PC-1 and ANK expression or activity. TNAP, PC-1 and ANK transgenic animals are useful animal models of human disorders. Thus, such animals are useful in screening for and identifying compounds for treating, ameliorating or reducing one or more symptoms associated with insufficient or deficient TNAP, PC-1 or ANK activity or expression, or treating, inhibiting or reversing hypo- or hyper-mineralization.

Thus, in accordance with the invention, there are also provided methods of identifying a compound useful in treating a disorder associated with insufficient or deficient TNAP, PC-1, ANK or OPN activity or expression, as well as methods of identifying a compound useful in treating, inhibiting or reversing hypo- or hyper-mineralization. In one embodiment, a method includes: providing an animal having deficient PC-1 or ANK activity or expression, wherein the animal has excessive mineralization in one or more tissues; administering a test compound that inhibits TNAP expression or an activity to the animal; determining if the animal exhibits an improvement in a tissue that has excessive mineralization, wherein an improvement in the tissue identifies the test compound as a compound useful in treating a disorder associated with insufficient or deficient PC-1 or ANK activity or expression. In another embodiment, a method includes: providing an animal having deficient PC-1 or ANK activity or expression, wherein the animal has excessive mineralization in one or more tissues; administering a test compound that increases OPN expression or an activity to the animal; determining if the animal exhibits an improvement in a tissue that has excessive mineralization, wherein an improvement in the tissue identifies the test compound as a compound useful in treating a disorder associated with insufficient or deficient PC-1 or ANK activity or expression. In another embodiment, a method includes: providing an animal having deficient TNAP activity or expression, wherein the animal has deficient mineralization in one or more tissues; administering a test compound that inhibits PC-1 or ANK expression or an activity to the animal; determining if the animal exhibits an improvement in a tissue that has deficient mineralization, wherein an improvement in the tissue identifies the test compound as a compound useful in treating a disorder associated with insufficient or deficient TNAP activity or expression. In various aspects, the transgenic animal is a mouse, having a PC-1 (Enpp1), TNAP (Akp2) or ANK (ank/ank) gene knockout, generated either by transgenic technology or that has occurred naturally.

Test compounds for use in the screening methods of the invention are found among biomolecules including, but not limited to: peptides, polypeptides, peptidomimetics, saccharides, fatty acids, steroids, purines, pyrimidines, derivatives, structural analogs or combinations thereof. Test compounds further include chemical compounds (e.g., small organic molecules having a molecular weight of more than 50 and less than 5,000 Daltons, such as hormones). Candidate organic compounds comprise functional groups necessary for structural interaction with proteins, particularly hydrogen bonding, and typically include at least an amine, carbonyl, hydroxyl or carboxyl group, preferably at least two of the functional chemical groups. The candidate organic compounds often comprise cyclical carbon or heterocyclic structures and/or aromatic or polyaromatic structures substituted with one or more of the above functional groups. Known pharmacological compounds are candidate test compounds that may further be subjected to directed or random chemical modifications, such as acylation, alkylation, esterification, amidation, etc., to produce structural analogs.

Test compounds can additionally be contained in libraries, for example, synthetic or natural compounds in a combinatorial library; a library of insect hormones is but one particular example. Numerous libraries are commercially available or can be readily produced; means for random and directed synthesis of a wide variety of organic compounds and biomolecules, including expression of randomized oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described herein.

All applications, publications, patents, other references, GenBank citations and ATCC citations mentioned herein are incorporated by reference in their entirety. In case of conflict, the present specification, including definitions, will control.

As used herein, the singular forms "a", "and," and "the" include plural referents unless the context clearly indicates otherwise. Thus, for example, reference to "a tissue" includes a plurality of such tissues and reference to "an inhibitor" includes reference to one or more such inhibitors, and so forth.

A number of embodiments of the invention have been described. Nevertheless, it will be understood that various modifications may be made without departing from the spirit and scope of the invention. Accordingly, the following examples are intended to illustrate but not limit the scope of invention described in the claims.

Example 1

Osteoblast Tissue-Nonspecific Alkaline Phosphatase Antagonizes and Regulates PC-1

Unless otherwise indicated, all chemical reagents were from Sigma-Aldrich (St. Louis, Mo.).

To indirectly determine the TNAP genotype of pups from our established breeding colony, we measured AP activity of mouse sera by colorimetric assay using p-Nitrophenyl Phosphate (pNPP) as substrate (Narisawa et al., *Dev. Dynamics* 208:432-446, 1997). Southern blot of tail tissue (Narisawa et al., *Dev. Dynamics* 208:432-446, 1997) was later used to confirm the genotype of each mouse.

Primary cultures of osteoblasts were isolated from calvariae of 1-4 day old pups that were hybrids of C57Bl/6×129/J mouse strains with wild-type, heterozygote and homozygote TNAP null genotypes. Isolation was performed by a slightly modified version of the time sequential collagenase technique described by Boonekamp et al. (*Proc. Kon. Ned. Akad. Wet.* B87:371-382, 1984). In brief, calvariae of the same genotype were pooled and three 10 minute incubations in 4 mM EDTA, 137 mM NaCl, 2.7 mM KCl, 3 mM $NaH_2PO_4$, pH 7.2, were performed, followed by seven 10 minute digestions in EDTA-free buffer, containing 180 units/ml collagenase type II (Worthington Biochemical Corporation, Lakewood, N.J.). All isolations were performed at 37° C. in a shaking water bath. The last five collagenase digestions, containing an enriched cell population of osteoblastic phenotype, were pooled and seeded at $4 \times 10^4$ cells/$cm^2$ in αMEM (Gibco BRL, Grand Island, N.Y.), containing 10% heat-inactivated FCS, penicillin (50 U/ml) and streptomycin (0.5 mg/ml).

To study mineralization, we used conditions under which we observed that osteoblasts normally formed von Kossa stain positive and alizarin red positive nodules at 7-10 days in culture. In brief, primary calvarial osteoblasts were cultured in complete αMEM media as described above, supplemented with β-glycerophosphate (10 mM) every third day and L-ascorbic acid (50 μg/ml) daily. MC3T3-E1 cells (Johnson et al., *J. Bone Min. Res.* 14:883-892, 1999) were maintained in the same medium, and for each experiment were plated at 80% confluence ($1 \times 10^6$ cells in a 10 cm tissue-culture plastic dish in 5 ml) and received β-glycerophosphate and L-ascorbic acid as for primary osteoblasts above.

For immunofluorescent staining/confocal microscopy to localize NTPPPH isozymes and AP, MC3T3 cells were cultured for up to seven days as described above. Cells were initially seeded on 18 $mm^2$ coverslips coated with poly D-lysine at a density of $3 \times 10^5$ cells/coverslip. At the indicated time points, cells were rinsed with PBS and fixed in 4% paraformaldehyde in PBS for 30 min at 22° C., and washed three times. Where indicated, cells were permeabilized with 0.1% Triton X-100 in blocking buffer for 10 minutes, and cells were again treated with blocking buffer for 45 minutes.

To detect AP activity, fixed cells were stained with a 1:1 solution of 0.2 mg/ml Naphthol AS-MX and 1.2 mg/ml Fast Red TR salt dissolved in 0.2 M Tris-HCl for 30 minutes in the dark at 25° C. This was followed by blocking (in PBS with 2% goat serum and 0.02% thiomersal) for 1 h. Where indicated, cells were permeabilized using 0.1% Triton X-100 in the blocking buffer for 15 min, followed by continued incubation in blocking buffer for another 45 min.

To detect PC-1 and B10, the murine anti-PC-1 alloantibody IR518 (42), or a rabbit antibody to the C-terminus (amino acids 580-875) of rat B10 (5), were diluted in blocking buffer and added to the cells for 18 hours at 4° C., washed 3× in PBS, and incubated with Alexa 488-conjugated goat anti-mouse IgG (Molecular Probes, Eugene, Oreg.), or goat anti-rabbit FITC (Sigma) at 1:400 in blocking buffer for 1 hour at 22° C. Coverslips were mounted with Slowfade media (Molecular Probes) and cells studied using a Zeiss Axiovert 100M laser scanning microscope using the FITC channel to detect PC-1 or B10 staining, and the Texas Red channel to detect AP staining.

For Western blotting, all samples were treated with lysis buffer (1% Triton X-100 in 0.2 M Tris base with 1.6 mM MgCl$_2$, pH 8.1) and protein concentration determined with the BCA protein assay (Pierce, Rockford, Ill.). Protein (0.03 mg) from each sample was separated by SDS-PAGE under reducing conditions and transferred to Nitrocellulose.

NTPPPH-specific, polyclonal antibodies to PC-1 (R1769) and B10 (Johnson et al., *J. Bone Min. Res.* 14:883-892, 1999; Johnson et al., *Arthritis Rheum.* 42:1986-1997, 1999) and rabbit antibody to tubulin (Sigma) served as primary antibodies in Western blotting, performed as described (Johnson et al., *J. Bone Min. Res.* 14:883-892, 1999; Johnson et al., *Arthritis Rheum.* 42:1986-1997, 1999). Washed nitrocellulose membranes were incubated with horseradish peroxidase (HRP)-conjugated secondary antibody in blocking buffer for 1 h, washed again, and immunoreactive products detected using the ECL system (Amersham, Arlington Heights, Ill.). Where indicated, semiquantitative analyses (of Western blots) were performed, using a previously described densitometry protocol (Johnson et al., *J. Bone Min. Res.* 14:883-892, 1999).

To specifically immunoprecipitate TNAP from osteoblast cell lysates we used a previously described method (Solan et al., *J. Bone Miner. Res.* 11: 183-192, 1996). We used a rabbit polyclonal antibody against rat TNAP that cross-reacts with mouse TNAP (Hoshi et al., *Histochem. Cell Biol.* 197:183-191, 1997).

For transfection studies, the cDNA expression constructs for wild-type human PC-1, and human B10 in pcDNA3.1 were as previously described (Johnson et al., *Arthritis Rheum.* 42:1986-1997, 1999). A 2.4 kb Hind II/Bgl II fragment from the human TNAP cDNA (ATCC #59635) was used as the template to generate the enzyme-deficient mutant by site-directed mutagenesis, as described by Tomic et al. (*Nucleic Acids Res.* 18:1656, 1990), using the primer 5'-CCAGGGT-TGTGGAGCTGACCCTTGAGGATGCAG-GCAGCCGTC-3' (SEQ ID NO: 1) to introduce the R54C substitution. The wild-type and mutant TNAP cDNAs were subcloned into pcDNA 3.1 expression vector (HindIII/SpeI) downstream from SV40 early promoter. Transient transfections were performed using 5 µg of plasmid DNA and Lipofectamine Plus (Life Technologies, Gaithersburg, Md.), as previously described, and this reproducibly achieved 40-45% transfection efficiency in osteoblastic cells in this study (Johnson et al., *Arthritis Rheum.* 42:1986-1997, 1999).

For MV mineralization assays, conditioned media from cultured cells were collected at the time points indicated, and initially centrifuged at 20,000×g for 20 minutes at 4° C. to pellet cellular debris, as previously described (Johnson et al., *J. Bone Min. Res.* 14:883-892, 1999). This was followed by centrifugation at 100,000×g for 1 hour to isolate the MV fraction, which was resuspended in Hanks' Balanced Salt solution (HBSS).

MV fractions (0.04 mg protein in 0.025 ml) were added in triplicate to 0.5 ml of "calcifying medium" (2.2 mM CaCl$_2$ (1 µCi/ml $^{45}$Ca), 1.6 mM KH$_2$PO$_4$, 1 mM MgCl$_2$, 85 mM NaCl, 15 mM KCl, 10 mM NaHCO$_3$, 50 mM N-Tris, and, where indicated, 1 mM ATP disodium salt, and/or 0.1% triton X-100, pH 7.6), and vortexed and incubated at 37° C. for 24 hours (Johnson et al., J. Bone Min. Res. 14:883(1999)). Samples were then centrifuged at 14,000×g for 10 min at 4° C. The pellet was washed twice with cold calcifying medium without ATP. The $^{45}$Ca in the mineral phase was solubilized in HCl and counted in 5 ml scintillation fluid.

The MV fraction of MC3T3 cells at 10 days in culture was assessed by conventional EM, using described methods (Bozzola and Russell, Electron Microscopy, Boston, Mass.: Jones and Bartlett, 1992). For specimen processing, we carried out double fixation (using 2% glutaraldehyde in cacodylate buffer, followed by 1% OsO$_4$ in H$_2$O), which was followed by dehydration in 2% uranyl acetate in 70% ethanol, and then in 100% ethanol, which was then followed by infiltration using acetonitrile/Epon (Bozzola and Russell, Electron Microscopy, Boston, Mass.: Jones and Bartlett, 1992).

For RT-PCR, total RNA was isolated using 0.5 ml TriZOL (Life Technologies, Gaithersburg, Md.) per 60 mm plate, with RNA extracted in chloroform and then precipitated in isospropanol overnight at −20° C. 600 ng of total RNA was reverse transcribed using 5 mM MgCl$_2$, 1×PCR buffer (200 mM Tris-HCl (pH 8.4), 500 mM KCl, 1.25 mM of each dNTP, 2.5 µM Oligo d(T) primer, 0.25 U/ml RNase Inhibitor (Sigma), 2.5 U/ml MuLV Reverse Transcriptase in a volume of 20 µl at 42° C. for 40 min, 99° C. 5 min, and 4° C. 5 min. One tenth of this reaction was used for a single round of RT-PCR, as previously described in detail (Johnson et al., *J. Bone Min. Res.* 14:883-892, 1999; Johnson et al., *Arthritis Rheum.* 42:1986-1997, 1999). Rodent B10 primers were sense 5'-TTAGCCACGGAGGAGCCCATTAAG-3' (SEQ ID NO:2) and antisense 5' AGCCTTGTAGTCAGTGCAG-CAGTC 3' (SEQ ID NO:3) (Andoh et al., Biochim. Biophys. Acta 1446:213-224, 1999), which amplified a 378 bp product at the 5' end of mouse B10 cDNA that hybridized to rat B10 cDNA in Southern blotting. Primers for mouse PC-1 and the ribosomal "housekeeping gene" L30 were as previously described and characterized (Johnson et al., *J. Bone Min. Res.* 14:883-892, 1999; Solan et al., *J. Bone Miner. Res.* 11:183-192).

PPi was determined by differential adsorption on activated charcoal of UDP-D-[6-$^3$H] glucose (Amersham, Chicago, Ill.) from the reaction product 6-phospho [6-$^3$H] gluconate, as previously described (Johnson et al., *Arthritis Rheum.* 42:1986 (1999)). PPi was equalized for the DNA concentration in each well, determined chromogenically following precipitation in perchlorate (Johnson et al., *Arthritis Rheum.* 42:1986(1999)). We determined specific activity of NTPPPH and AP, by previously described assays (Johnson et al., *Arthritis Rheum.* 42:1986(1999)). Units of NTPPPH and AP were designated as µmoles of substrate hydrolyzed per hour (per µg protein in each sample).

To measure transglutaminase activity, we added 30 µg of protein in 0.08 ml of 5 mM Tris HCl (pH 7.5), 0.25 M sucrose, 0.2 mM MgSO$_4$, 2 mM DTT, 0.4 mM PMSF, 0.4% Triton X-100 to an equal volume of 300 mM Tris HCl, pH 7.5, 10 mM CaCl$_2$, 20 mM DTT, 10 mg/ml N,N' dimethyl-casein and 10 µCi/ml [$^3$H] putrescine (15) for 30 minutes at 37° C. The reaction was stopped by adding cold 10% TCA and 0.5% tannic acid. The precipitate was washed with 10% TCA and 0.25% tannic acid. The pellet was resuspended in 0.1 ml 1 M NaOH. Samples were then treated with 2% H$_2$O$_2$ for 4 hours at 22° C. followed by 4 hours of treatment at 40° C., and then counted for 5 minutes in 5 ml of scintillation fluid. Transglutaminase activity was designated as nanomoles of putrescine incorporated into casein (per mg protein in each sample).

Where indicated, error bars represent SD. Statistical analysis was performed using the Student's t test (paired 2-sample testing for means), applied on Microsoft Excel 5.0 for the Macintosh computer.

Extravesicular ATP-dependent extension of mineral deposition is impaired in MVs from patients with perinatal hypophosphatasia (Anderson et al., *Am. J. Pathol.* 151:1555-1561, 1997). We prepared MV fractions from osteoblastic cells as described above and visualized MVs in such fractions that had characteristic morphology and size, mainly 100-200 nm in diameter. Nearly all the MVs had intact membranes. Many MVs had the capacity to develop electron-dense internal deposits consistent with crystals. We first assessed the ability of murine heterozygous and homozygous TNAP-deficient osteoblast MV fractions to precipitate calcium. In doing so, aliquots of the MV fractions were treated, where indicated, with the detergent Triton X-100 (0.1%), which is capable of enhancing ATP-initiated MV mineralization via MV membrane perturbation (under conditions where such treatment does not modulate MV enzyme activities) (Hsu et al., *Biochim. Biophys. Acta* 1416:320-332, 1999).

MV fractions were collected from pooled conditioned media at the time periods in culture indicated, from primary calvarial osteoblasts of different (n=12 each) wild-type (+/+), TNAP heterozygous (+/−) and homozygous knockout (−/−) mice, cultured as described above in medium supplemented with β-glycerophosphate and ascorbate. MV fractions (0.04 mg protein in 0.025 ml HBSS) were added to 0.5 ml of the calcifying medium described above, with or without the presence of 1 mM ATP, and/or 0.1% Triton X-100, at pH 7.6, vortexed and incubated at 37° C. for 24 hours. After centrifugation, the pellet was washed and counted for $^{45}$Ca in the mineral phase, as indicated above. Background ATP-independent $^{45}$Ca precipitation for detergent-treated MV fractions was not significantly different from the results without detergent treatment. n=5, p<0.001 for TNAP−/− vs. TNAP+/+ at 3-6 days and 6-10 days in Triton-treated MV fractions with ATP present. In the absence of detergent treatment, TNAP-deficient osteoblasts and control osteoblasts released MV fractions that were comparably able to precipitate calcium in an ATP-dependent manner. However, treatment of the MV fractions with Triton X-100 unmasked a significant defect in the ATP-dependent calcium-precipitating ability of TNAP−/− osteoblast-derived MV fractions relative to TNAP+/+ MV fractions. The defect directly correlated with the extent of TNAP deficiency, because it was greater in MV fractions derived from TNAP−/− mice than from TNAP+/− mice. The defect was exposed by using ATP as a substrate and was active at the level of the MV fractions. Because NTPPPH activity hydrolyzes ATP and is associated with MVs, we assessed NTPPPH expression in osteoblasts and osteoblast-derived MV fractions.

Total RNA isolation and RT-PCR analysis were performed to determine whether PC-1 and B10 mRNA were expressed in cultured MC3T3 cells and primary calvarial osteoblasts from TNAP wild-type, heterozygotic and homozygous knockout mice. Cells were cultured for the number of days indicated, and as described above. Assay of the ribosomal "housekeeping gene" L30 served as the control for RNA loading. Both PC-1 and B10 mRNA expression was consistently detected by RT-PCR in cultured primary calvarial osteoblasts isolated from TNAP+/+ mice and from TNAP+/− and TNAP−/− mice. In addition, PC-1 and B10 mRNA expression were both detected in MC3T3 cells, which were grown under the same mineralizing conditions used for primary calvarial osteoblasts.

Primary calvarial osteoblasts from TNAP+/+, and +/− and −/− mice were cultured and MV fractions isolated as described above. Then 30 µg of protein from cell lysates (at days 6 and 10 in culture) and MV fractions (at day 10) were analyzed by SDS-PAGE and Western blotting as described above. In addition, MC3T3 cells were cultured with or without transfection with empty plasmid, or PC-1 or B10 in pcDNA3.1, as indicated, using the procedure described above. Cell lysates and MV fractions (30 µg of protein) were studied by Western blotting after isolation at day 7 in culture. PC-1 protein expression also was readily detected in cell lysates and in the MV fractions of primary calvarial osteoblasts of TNAP+/+ mice, and of TNAP+/− and TNAP−/− mice. However, PC-1 was more readily detected in equal amounts of protein from MV fractions of the osteoblasts of TNAP+/+ mice than TNAP−/− mice. PC-1 and B10 both were detected in cell lysates of primary calvarial osteoblasts and MC3T3 cells. In contrast, in MV fractions from calvarial osteoblasts of all mice tested, B10 was below the limits of detection in Western blotting, and B10 could not be detected in MV fractions of MC3T3 cells. Semiquantitative densitometric analyses of these Western blot findings suggested a greater than 8 fold increase in MV fraction PC-1 in MV fractions from TNAP+/+ compared to TNAP−/− mice, and levels of cell lysate PC-1 more than 50% greater in TNAP+/+ cells than in TNAP−/− cells, under conditions where tubulin was not greater in cells of TNAP+/+ mice compared to TNAP−/− mice.

Because we detected PC-1 but not B10 expression in MV fractions of primary calvarial osteoblasts and MC3T3 cells, we assessed if direct up-regulation of B10 expression would be associated with localization of B10 in MV fractions. To do so, we transfected MC3T3 cells with human PC-1 and B10 cDNAs, which are approximately 80% identical to their respective rodent homologues (Fedde et al., *Am. J. Hum. Genetics* 47:776(1990)). We cultured the MC3T3 cells under mineralizing conditions as used for primary calvarial osteoblasts.

Transfection of PC-1 increased immunoreactive PC-1 in MC3T3 cells and elevated both cell-associated and MV fraction NTPPPH activity in MC3T3 cells. PC-1 also significantly elevated MV fraction PPi, but not extracellular PPi, suggesting enrichment of PC-1 in the MV fractions. In contrast, transfection of B10 elevated cell-associated NTPPPH activity but did not augment MV fraction NTPPPH activity in MC3T3 cells. B10 transfection also did not elevate MV fraction PPi. Transfected MC3T3 cells demonstrated an increase of PC-1 or B10 protein, but only PC-1 was detectable by Western blotting in MV fractions derived from the cells transfected with either NTPPPH.

Because PC-1 but not B10 appeared to localize in isolated osteoblast-derived MV fractions, we assessed and compared the distribution of PC-1 and B10, relative to TNAP, in mineralizing MC3T3 cells, using confocal microscopy. Prior to matrix mineralization, at 48 hours in culture, TNAP staining was readily detected on the surface of the subconfluent MC3T3 cells. Surface PC-1 and B10 immunostaining were weak at this point in time. Permeabilization of MC3T3 cells revealed that B10 staining was predominantly intracellular at 48 hours.

At 7 days in culture, when mineralization of the matrix by confluent MC3T3 cells was detectable, PC-1 and TNAP staining co-localized in broad areas of the pericellular matrix. Osteoblast surface and pericellular matrix B10 staining remained weak at this time. Moreover, permeabilization of the MC3T3 cells revealed that B10 staining remained predominantly intracellular in MC3T3 cells in a distribution distinct from that shared by PC-1 and TNAP.

Our results revealed that TNAP and PC-1 were co-expressed and co-localized in mineralizing osteoblastic cells and their MV fractions and pericellular matrix. Thus, we concluded this study by directly assessing the relationship between TNAP and PC-1 functions in MV fractions. To do so, we first transfected MC3T3 cells with cDNAs encoding wild-type TNAP and the [R54C] catalytically inactive mutant of TNAP.

Transfection of wild-type TNAP significantly elevated cell-associated and MV fraction-associated AP activity in MC3T3 cells and decreased the PPi associated with MV fractions derived from MC3T3 cells transfected with PC-1.

Paradoxically, transfection of wild-type TNAP was associated with a significant increase in cell-associated NTPPPH, and an even greater increase in MV fraction-associated NTPPPH activity in MC3T3 cells, but no significant change in activity of transglutaminase activity, which served as a control enzyme for these experiments. We established that this result was not attributable to intrinsic NTPPPH activity of TNAP. Specifically, immunoprecipitation of TNAP from osteoblast cell lysates isolated >85% of the TNAP activity, but was not associated with any co-immunoprecipitation of NTPPPH activity (starting mean cell lysate NTPPPH 1.7 Units, and alkaline phosphatase 4.3 Units; beads after immunoprecipitation with antibody to TNAP had mean of 0.09 Units NTPPPH and 4.1 Units alkaline phosphatase; beads after immunoprecipitation with antibody to PC-1 had mean of 1.3 Units NTPPPH and 0.11 Units alkaline phosphatase, n=5).

Because TNAP appeared to regulate the NTPPPH activity of osteoblastic MC3T3 cells, we assessed if this effect was dependent on TNAP enzymatic activity. Wild-type TNAP, but not the enzyme-inactive mutant of TNAP induced an increase in both MV fraction NTPPPH and AP_activity. In contrast to wild-type TNAP, the mutant TNAP failed to decrease MV fraction PPi.

Our results indicated that immunoreactive PC-1 decreased progressively over time in culture in TNAP−/− osteoblasts relative to primary osteoblasts from TNAP+/− and TNAP+/+ mice. Thus, we also assessed the relationship between TNAP deficiency, and MV fraction PPi-generating NTPPPH activity and PPi concentration in primary osteoblasts.

Cell-associated NTPPPH but not transglutaminase activity progressively decreased over time in culture in osteoblasts from TNAP−/− mice, relative to cells from TNAP+/− and TNAP+/+ mice, and was significantly less in TNAP−/− cells than in TNAP+/+ cells at 14 days. Moreover, NTPPPH activity but not transglutaminase activity was significantly lower in MV fractions derived at days 10-13 from TNAP−/− mice in comparison to MV fractions from osteoblasts of TNAP+/+ animals, with the values for MV fraction NTPPPH activity being intermediate for TNAP+/− osteoblasts. Despite the presence of the lowest MV fraction NTPPPH specific activity, it was in the TNAP−/− state that the highest MV fraction-associated concentration of the mineralization inhibitor PPi was observed.

Last, we directly assessed the effects of TNAP, PC-1 and B10 on MV fraction-mediated mineralization. Transfection of PC-1, but not B10, significantly inhibited ATP-dependent calcium precipitation by MV fractions (detergent-treated and untreated) isolated from the transfected MC3T3 cells. Wild-type but not mutant TNAP significantly antagonized the inhibitory effect of PC-1 on calcium precipitation by MV fractions derived from the MC3T3 cells. Thus, TNAP functioned to directly antagonize the inhibitory effect of PC-1 on the mineralizing activity of osteoblast-derived MV fractions.

Definition of the function of TNAP is pivotal to understanding how the skeleton mineralizes. We previously demonstrated that PC-1 suppressed osteoblast MV-mediated mineralization under conditions where sodium phosphate was provided as the major phosphate source for hydroxyapatite formation (Johnson et al., *J. Bone Min. Res.* 14:883-892, 1999). The current study employed β-glycerophosphate, which, to provide free phosphate, requires hydrolysis by inorganic phosphatase activity such as that exerted by TNAP. PC-1 markedly inhibited ATP-dependent calcium precipitation by MV fractions under these conditions in this study. We also demonstrated that TNAP and PC-1 were concomitantly expressed, and TNAP and PC-1 co-localized both in cultured osteoblasts that formed mineralized nodules, and the MV fractions derived from the mineralizing cells.

TNAP functioned to directly antagonize the inhibitory effects of PC-1 on ATP-dependent precipitation of calcium by MV fractions. In this regard, a forced increase in TNAP localization in MV fractions diminished basal MV fraction-associated PPi and prevented PC-1 from augmenting MV fraction PPi. Our results suggest that TNAP promotes MV-mediated mineralization in large part by hydrolyzing the MV-associated mineralization inhibitor PPi generated by PC-1 through catabolism of exogenous ATP.

A selective impairment of extravesicular propagation of hydroxyapatite by ATP-treated MVs has been demonstrated in subjects with perinatal hypophosphatasia (Anderson et al., *Am. J. Pathol.* 151:1555-1561, 1997). This suggested the possibility of defective metabolism of PPi at the exterior face of MVs. In previous studies the majority of both NTPPPH activity (Ryan and McCarty, *Ann. Rheum. Dis.* 54:939-941, 1995) and TNAP activity (Anderson, *Clin. Orthopaed. Rel. Res.* 314:266-280, 1995; Hsu et al., *Int. J. Biochem.* 25:1737-1742, 1993) have been found to be active on the external face of MVs. We did not directly assess surfaces where the enzyme activities were localized in the MVs obtained in the current study. The observation that detergent-induced perturbation of MV fractions was required to reveal a defect in ATP-dependent MV calcium precipitation associated with TNAP deficiency could be consistent with external face orientation of TNAP enzyme activity and/or release of a mineralization inhibitor such as PPi from MVs.

Significantly, a mineralizing defect correlated directly with the extent of TNAP deficiency measured in osteoblast-derived MV fractions. In contrast, the total concentration of MV fraction-associated PPi was less clearly related to the mineralizing defect observed in TNAP+/− and TNAP−/− osteoblasts. The finding that MV fractions from TNAP+/− and TNAP−/− osteoblasts both demonstrated a mineralizing defect may help explain in vitro differences in mineralization between osteoblasts from TNAP+/− and TNAP+/+ mice. Specifically, when comparing TNAP+/− and TNAP+/+ mice at day 2-3 after birth, no morphologic differences could be detected in the bones in vivo. However, initiation of mineralization in vitro was delayed in the TNAP+/− osteoblast cultures. In this regard, in vitro cultures evaluated at different time points (days 4, 6, 8) revealed a delayed increase in TNAP activity in the TNAP+/− cultures compared to TNAP+/+ cultures, accompanied by a later onset of mineralization, as demonstrated by von Kossa staining and measurement of deposited calcium$_1$.

We speculate that the foci in which PPi might be concentrated at MVs may be more critical in regulating mineralization than the total PPi concentration associated with MVs. Alternatively, our results suggest that PPi is not likely to be the sole potent inhibitor of MV mineralization in normal or TNAP deficient states. For example, the ability to precipitate calcium dramatically declined for MV fractions of normal primary calvarial osteoblasts recovered at days 10-13 in culture, when much of the mineralization of nodules had already been completed. In contrast, the concentration of PPi associated with MV fractions changed little over 13 days in culture of the normal calvarial osteoblasts.

The relative stability of PPi in MV fractions produced at various time points may reflect parallel changes in MV AP and NTPPPH activity observed in normal osteoblasts. Significantly, TNAP expression directly promoted an increase in MV fraction NTPPPH specific activity in MC3T3 cells in this study. Moreover, TNAP-expressing primary calvarial osteoblasts ultimately produced MV fractions with significantly more NTPPPH activity than MV fractions produced by TNAP-deficient osteoblasts. Our results suggested that TNAP, by an enzyme activity-dependent mechanism, acts to control mineralization in part by modulating the content of its own inhibitor in osteoblasts and osteoblast-derived MVs. It will be of interest to determine if modulation of PPi concentration at a specific location is a regulatory signal for PC-1 gene expression or the distribution of PC-1 to the plasma membrane and MVs. Alternatively, transphosphorylation reactions catalyzed by TNAP (Whyte, Endocrine Rev. 15:439-461, 1994) might be responsible for modulating MV composition in osteoblasts (Anderson, Clin. Orthopaed. Rel. Res. 314:266-280, 1995).

MV constituents include matrix proteins and proteoglycans, calcium binding proteins and phospholipids, metalloproteinases, and transglutaminase activity (Anderson, Clin. Orthopaed. Rel. Res. 314:266-280, 1995; Bosky, Conn. Tissue Res. 35:357-363, 1996; Boskey et al., Calcif. Tiss. Int. 60:309-315, 1997; Hsu and Anderson, J. Biol. Chem. 271: 26383-26388; Rosenthal et al., Arthritis Rheum. 40:966-970, 1997). Transglutaminase activity can promote mineralization by promoting activation of latent TGFβ (Kojima et al., J. Cell. Biol. 121:439-448, 1993), and modifying extracellular matrix proteins including osteonectin (Aeschlimann et al., J. Cell Biol. 129:881-892, 1995). However, osteoblast MV fraction transglutaminase activity did not change in response to direct TNAP transfection of MC3T3 cells, and there was only a non-statistically significant trend to higher transglutaminase activity in MV fractions of TNAP-deficient osteoblasts. It will be of interest to determine what other constituents of MVs that regulate mineralization are modulated by TNAP activity in osteoblasts.

We have demonstrated that PC-1 preferentially distributed to osteoblast MV fractions, in comparison to the closely related NTPPPH B10. MV fraction-associated NTPPPH and PPi were increased by a direct elevation in expression of PC-1 but not of B10. The ability of PC-1 to suppress MV-mediated mineralization was not shared by B10. We observed that B10 remained in a predominantly intracellular distribution distinct from that of PC-1 and TNAP in mineralizing osteoblastic cells. These findings help explain how osteoblast-mediated hyperossification occurs in PC-1 deficient mice, despite the fact that mouse osteoblasts also contain abundant B10, and despite the physiologic expression (as a component of BMP-2-mediated chondro-osseous differentiation) of a distinct PDNP/NTPPPH isozyme called autotaxin, which is a predominantly secreted species (Bachner et al., Mech. Develop. 84:121-125, 1999).

The genes for PC-1 and B10 are located in close proximity on chromosome 6q21-23, presumably reflecting an antecedent gene duplication event (Goding et al., Immunol. Reviews 161:11-26, 1998). Each gene encodes a class II (intracellular N-terminus) transmembrane glycoprotein of 120-130 kDa that shares a highly homologous extracellular domain containing 2 somatomedin B-like regions and a conserved catalytic site (Goding et al., Immunol. Reviews 161:11-26, 1998). However, B10 has a unique extracellular RGD cell adhesion motif, and the cytosolic tails of PC-1 and B10 share no significant homology (Goding et al., Immunol. Reviews 161:11-26, 1998). Moreover, differential localization and function of PC-1 have been observed in other tissues. For example, PC-1 translocates to the basolateral surface and B10 to the apical surface in a polarized cell type (hepatocytes), an effect attributed to differences in the cytosolic tail (Scott et al., Hepatol. 25:995-1002, 1997). Furthermore, PC-1 but not B10 preferentially localizes to the plasma membrane in human articular chondrocytes and only PC-1 causes an increase in extracellular PPi in these cells (Okawa et al., Nature Genetrics 19:271-273, 1998).

In conclusion, TNAP promotes mineralization in part by removing the profound inhibitory effect of PC-1-generated PPi on ATP-dependent MV-mediated mineralization. It will be of interest to determine if TNAP does so by not only hydrolyzing PPi but also by dephosphorylating ATP that would otherwise be used by PC-1 to generate PPi. This study established that PC-1 preferentially distributed to osteoblast MV fractions in comparison to another NTPPPH isozyme B10 (also known as PDNP3). It will be of interest to determine if the signals responsible for PDNP/NTPPPH-selective basolateral membrane localization of PC-1 in polarized epithelia and PC-1 distribution to MVs are the same or different. Results of such studies would help elucidate how selective concentration of specific ecto-enzymes occurs in MVs. We also conclude that TNAP up-regulates the amount of NTPPPH expressed by osteoblasts, which influences the amount of NTPPPH activity distributing to osteoblast MVs. Once their bone-making duties in the basic multicellular unit of bone are completed, the majority of osteoblasts must become less active in bone formation (Manolagas and Weinstein, J. Bone Mineral Res. 14:1061-1066, 1999). We speculate that the control of PC-1 expression by TNAP may be one of the physiologic means by which normal osteoblasts regulate their bone-making activity.

The association of osteomalacia with TNAP deficiency (hypophosphatasia) has illustrated the essential function of TNAP in osteoblastic bone matrix mineralization. TNAP acts on multiple substrates and has several potential physiologically significant functions in mineralization. However, the ability of TNAP to hydrolyze PPi to Pi has been hypothesized to be central to the ability of TNAP to promote osteoblastic mineralization. This study indicated that TNAP has at least one native antagonist, the NTPPPH PC-1, which hydrolyzes ATP to generate PPi, an inhibitor of osteoblast MV-mediated mineralization. The results of this study indicated that PC-1 (but not another NTPPPH isozyme B10/PDNP3) acts as a mineralization inhibitor at the level of MVs. PC-1 has the potential to inhibit osteoblastic mineralization not only by generating PPi associated with MVs but also by hydrolyzing ATP that may be used in part by MV TNAP to mineralize. Our results suggested that TNAP acts to promote mineralization in part by removing the profound inhibitory effect of PC-1-generated PPi on ATP-dependent MV-mediated mineralization. Whether TNAP effects are mediated not only by PPi hydrolysis but also by TNAP-induced dephosphorylation of the PC-1 substrate ATP will be of interest to further investigate. One surprising finding of this study was that TNAP modulated the expression of its own antagonist PC-1 in osteoblasts, which was associated with changes in the distribution to osteoblast MV fractions of NTPPPH activity. Finally, in view of the association of deficient PC-1 expression with hyperossification in vivo, the results of this study suggest the testable hypothesis that a marked attenuation of PC-1 expression in vivo may have the potential to augment bone matrix mineralization in the setting of TNAP deficiency.

Example 2

Figures 1A, 1B, 1C, 2A, 2B, 2C:
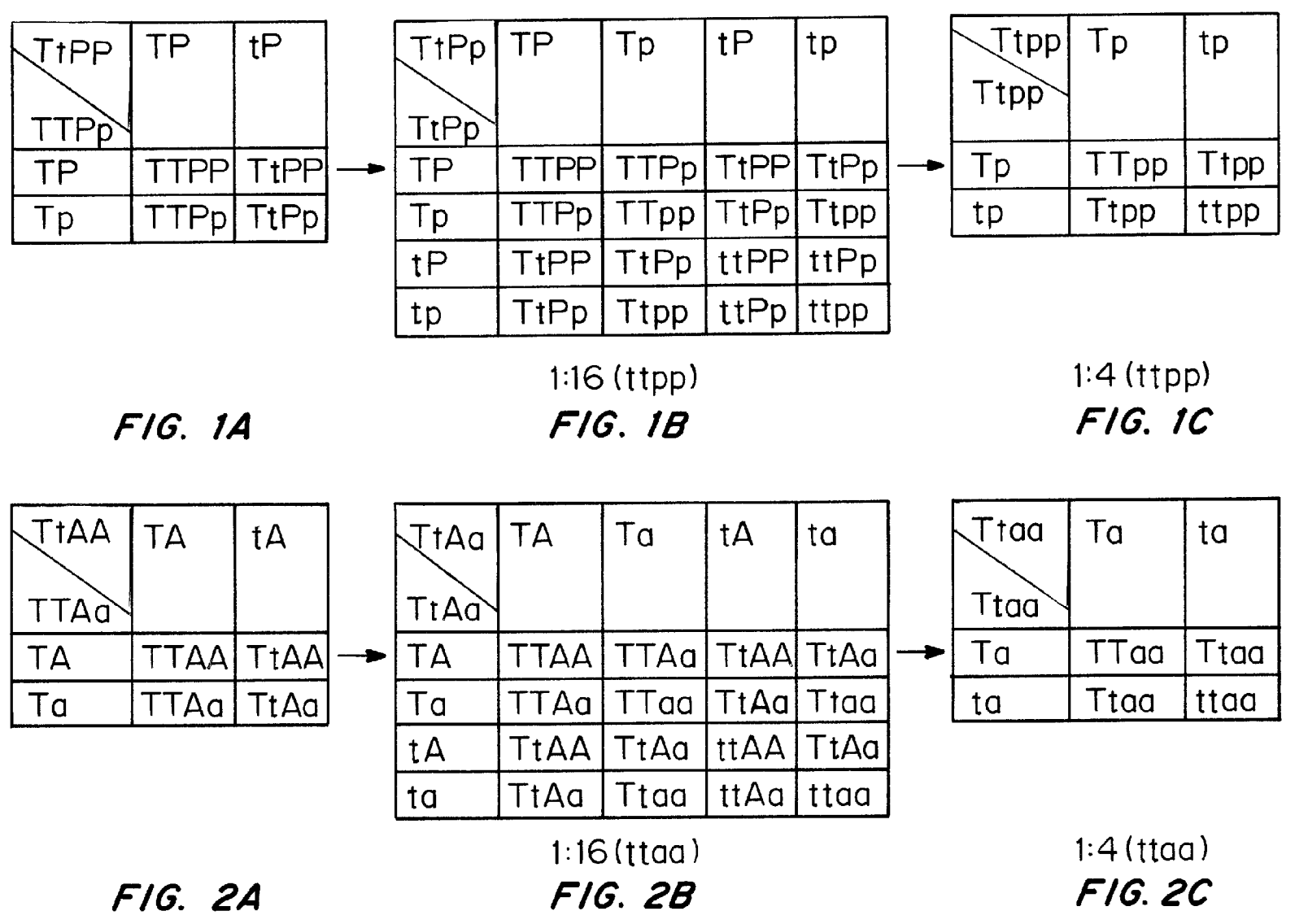

Crossbreeding to Produce Mice that are Heterozygous for the TNAP Knock-Out and the PC-1 Knockout Crossbreedings is performed to match the TNAP knock-out and the PC-1 knock-out mice in order to obtain mice that are heterozygous for both genes. These double heterozygous mice are used as a source of tissue as well as primary osteoblastic cells to examine bone mineralization parameters and compared them to those obtained for the TNAP or PC-1 single gene defects. These double heterozygous mice are also used for breeding experiments in order to obtain mice that are homozygous for a PC-1 mutation but heterozygous for the TNAP mutation {[TNAP+/−; PC-1−/−] or (Ttpp)}. We expect these mice to be born alive and display an amelioration of the bone abnormalities. These breedings also produce mice that are double homozygous for a TNAP and a PC-1 mutation, i.e., [TNAP−/−; PC−−/−] or (ttpp) in FIG. 1B at an average ratio of 1 in 16 born pups if the double mutations is not lethal in utero.

The following genotypes are analyzed for phenotypic abnormalities: Ttpp, ttpp and ttpp. Mice with these genotypes are analyzed exhaustibly as to their bone mineralization abnormalities in vivo as well as in cultures of primary osteoblasts. After achieving step B of the breedings, sufficient number of mice are obtained that are heterozygous for TNAP (Ttpp) and homozygous mutant for PC-1 (Ttpp), enabling us to obtain ttpp mice using fewer animals and fewer breedings as per the schematic in FIG. 1C.

Example 3

Crossbreeding to Produce Mice that are Heterozygous for the TNAP Knock-Out and the ank Deficiency Crossbreedings is performed to match the TNAP knock-out and the ank-deficient mice in order to obtain mice that are heterozygous for both genes as examplified in FIG. 2A. These double heterozygous mice are used as a source of tissue as well as primary osteoblastic cells to examine bone mineralization parameters and compared them to those obtained for the TNAP or ANK single gene defects. These double heterozygous mice are also used for breeding experiments in order to obtain mice that are homozygous for a ank mutation but heterozygous for the TNAP mutation {[TNAP+/−; ank/ank] or (Ttaa) in FIG. 2B}. We expect these mice to be born alive and display an amelioration of the bone abnormalities. These breedings also produce mice that are double homozygous for a TNAP and an ank mutation, i.e., {[TNAP−/−; ank/ank] or (ttaa) in FIG. 2B} at an average ratio of 1 in 16 born pups if the double mutation is not lethal in utero. The following genotypes are analyzed for phenotypic abnormalities: Ttaa, ttAa and ttaa. Mice with these genotypes are analyzed exhaustibly as to their bone mineralization abnormalities in vivo as well as in cultures of primary osteoblasts. After achieving step B of the breedings a sufficient number of mice are obtained that are heterozygous for TNAP (Ttaa) and homozygous ank mutants (Ttaa) to enable us to obtain ttpp mice using fewer animals and fewer breedings as per the scheme in FIG. 2C.

Example 4

Calvarial Osteoblasts

Calvarial osteoblasts are isolated in order to measure parameters of bone mineralization. Newborn pups are anesthetized and decapitated at 2-3 days of age for isolation of the calvarial bone to be used either immediately or frozen down. Blood obtained at the time of sacrificing the mice is used to type the pups as being homozygous or heterozygous (based on the respective plasma levels of TNAP) to enable us to pool the isolated homozygous (respectively heterozygous) calvaria for the osteoblast isolation. Primary osteoblasts are then be stored frozen until the time of use during which time the genotype for TNAP, PC-1 and/or ANK is established by Southern blot analysis.

Example 5

Lack of Alkaline Phosphatase (TNAP) in Bone Leads to Osteomalacia (Rickets) and Infantile Hypophosphatasia in Mice Mice deficient in the TNAP gene mimic the most severe forms of hypophosphatasia, i.e., perinatal and infantile hypophosphatasia. These TNAP−/− mice are growth impaired, develop epileptic seizures, apnea, and die before weaning with evidence of cranial and pulmonary hemorrhages. Examination of the tissues indicate abnormal bone mineralization, morphological changes in the osteoblasts, aberrant development of the lumbar nerve roots, disturbances in intestinal physiology, increased apoptosis in the thymus and abnormal spleen.

As in human patients, there is a striking elevation of pyrophosphate (PPi) in the urine of the TNAP knock-out mice, elevated levels of urinary phosphoethanolamine and a striking accumulation of plasma pyridoxal-5'-phosphate. Skeletal preparations of embryos and newborns revealed no differences between the TNAP+/+, TNAP+/− and TNAP−/− mice. However, the staining of 8-day old TNAP−/− bones clearly showed poor mineralization in the parietal bones, scapulae, vertebral bones, and ribs. Evidence of spontaneous fractures was evident in the fibulae. Fractures in the rib bones and broken incisors were also observed. The bone abnormalities worsen progressively with age as shown radiographically.

Example 6

Primary Cultures of TNAP Knock-Out (Ko) Osteoblasts

To evaluate the ability of primary osteoblasts to form and mineralize bone nodules in vitro, wild-type (wt), heterozygous and knock-out (ko) osteoblasts were cultured in media supplemented with ascorbic acid, using β-glycerophosphate as phosphate source. At different time points (day 4, 6 and 8), cultures were fixed and stained with the von Kossa procedure to visualize mineralized nodules. Staining of post-confluent cultures of TNAP ko osteoblasts showed that these cells were able to form cellular nodules, typical of long-term calvarial osteoblast cultures. However, in contrast to cultures of TNAP positive osteoblasts, mineralization by TNAP−/− osteoblasts was never initiated. Similar results were found using ATP as phosphate source. Calcium measurements further confirmed the lack of mineral deposition in these TNAP ko cultures. The amounts and sizes of the nodular structures did not vary significantly between the different genotypes, only mineralization of the nodules appeared to be affected by the lack of TNAP. Of particular interest is the finding that initiation of mineralization was delayed in the TNAP heterozygous osteoblast cultures compared to wt osteoblasts. This was correlated with a delayed increase in the levels of TNAP activity in TNAP+/− in comparison with TNAP+/+ osteoblasts. The extent of bone mineral deposition in these cultures was confirmed by quantifications of deposited calcium. These results were compatible with the von Kossa stainings, showing clear phenotypic differences between wt, heterozygous and ko osteoblasts concerning bone nodule mineralization. Mineralization of ko osteoblast cultures could be restored by exposure to conditioned media from wt osteoblast cultures. This mineralization was induced both by untreated conditioned media and by media that had been ultracentrifuged to exclude matrix vesicles. Mineralization was also induced by adding purified soluble recombinant human TNAP enzyme to the ko osteoblast culture medium. As in control cultures, the deposition of mineral in these cultures was restricted to bone nodules. In contrast, neither heat-inactivated recombinant TNAP, nor enzymatically inactive mutants of TNAP, such as [R54C]TNAP or [V365I]TNAP, were able to induce mineralization.

These data indicate that a certain level of TNAP activity has to be reached for calcium deposition to be initiated. Enzymatic disorders are usually inherited in a recessive pattern, suggesting that one functional allele is enough to maintain a healthy phenotype. However, in hypophosphatasia, cases of suggested autosomal dominant transmission have been discussed. Our data indicate that a limited decrease of TNAP activity might be sufficient to cause phenotypic abnormalities by affecting the rate of mineralization. In a recent publication, Zurutuza et al. (*Hum. Mol. Genet.* 8:1039-1046, 1999) showed the phenotypic heterogeneity of hypophosphatasia to be correlated to the nature of the mutations. While severe alleles, often present in lethal forms of hypophosphatasia, had mutations in, e.g., the active site resulting in little if any AP activity, moderate alleles carried mutations in less conserved regions of the enzyme, maintaining substantial activity. Our data indicate that even a minor reduction in the levels of expression of AP protein and enzyme activity can be sufficient to impair the mineralization process and cause dominant phenotypic abnormalities in some cases of hypophosphatasia.

Example 7

Abnormalities in the Metabolism of the Natural Substrate Pyridoxal-5'-Phosphate (Vitamin B6) Explain Many of the Phenotypic Abnormalities in Hypophosphatasia but not the Abnormal Bone Defects At the time that we were developing the TNAP knock-out mice, Waymire et al. (*Nature Genet.* 11:45-51, 1995) independently reported the production of TNAP knock-out mice. Their results indicated that vitamin B6 administration could partially rescue the epileptic seizures in these mice, concomitantly prolonging their life. These studies provided support to the hypothesis, set forth by Michael P. Whyte in his studies of human hypophosphatasia, that pyridoxal-5'-phosphate (vitamin B6) might be a natural substrate of TNAP. The rationale for this hypothesis is that pyridoxal-5'-phosphate cannot easily traverse biological membranes but that the related, more hydrophobic derivatives, pyridoxal and pyridoxamine can do so with much better kinetics. Thus, the presumption is that the cells that are deficient in TNAP cannot dephosphorylate pyridoxal-5'-phosphate on the outside of the cells leading to an intracellular deficiency of Vitamin B6 (Whyte, *Endocrine Rev.* 15:439-461, 1994). Prompted by these findings, we performed the following treatments: Administration of exogenous pyridoxal HCl delayed the onset of epileptic attacks and increased the life span also in our TNAP-/- mice. The episodes of apnea ceased and myelinization of lumbar nerve roots improved. However, hypomineralization and accumulation of osteoid continued to worsen with age. Control mice fed a vitamin B6-depleted diet developed epileptic seizures indistinguishable from those observed in TNAP-/- mice, abnormal apoptosis in the thymus and thinning of the nerve roots. These vitamin B6-depleted mice, however, showed neither evidence of bone mineralization abnormalities in vivo nor in vitro upon testing primary cultures of osteoblasts. These results indicate that, while abnormal metabolism of vitamin B6 explains many of the abnormalities in this mouse model of infantile hypophosphatasia, it is not the basis of the abnormal mineralization that characterize this disease. The bone abnormalities are due to inappropriate regulation of inorganic pyrophosphate (PPi) levels as suggested by our experiments as described below.

Example 8

Impaired ATP-Dependent Calcium Precipitation by Detergent-Treated Osteoblast-Derived MV Fractions of TNAP-Deficient Mice A selective impairment of extravesicular propagation of hydroxyapatite by ATP-treated MVs has been demonstrated in subjects with perinatal hypophosphatasia (Anderson et al., *Am J. Pathol.* 151:1555-1561, 1997). This suggested the possibility of defective metabolism of PPi at the exterior face of MVs. In previous studies the majority of both NTPPPH activity (Clair et al., *J. Biol. Chem.* 272:996-1001, 1997) and TNAP activity (Rachow et al., *Rheum. Dis. Clin. N. Am.* 14:289-302, 1988) have been found to be active on the external face of MVs. Our own studies to define the location of TNAP on the surface of MVs by immunoelectron microscopic studies is consistent with this view.

We assessed the ability of heterozygous and homozygous TNAP-deficient osteoblast MV fractions to precipitate calcium. In doing so, aliquots of the MV fractions were treated with the detergent Triton X-100 (0.1%), which is capable of enhancing ATP-initiated MV mineralization via MV membrane perturbation (under conditions where such treatment does not modulate MV enzyme activities) (Hsu et al., *Biochim. Biophys. Acta* 1416:320-332, 1999). In the absence of detergent treatment TNAP-deficient osteoblasts and control osteoblasts released MV fractions that were comparably able to precipitate calcium in an ATP-dependent manner. However, treatment of the MV fractions with Triton X-100 unmasked a significant defect in the ATP-dependent calcium-precipitating ability of TNAP-/- osteoblast-derived MV fractions relative to TNAP+/+ MV fractions. The defect directly correlated with the extent of TNAP deficiency, because it was greater in MV fractions derived from TNAP-/- mice than from TNAP+/- mice.

Cell-associated NTPPPH decreased over time in culture in osteoblasts from TNAP-/- mice, relative to cells from TNAP+/- and TNAP+/+ mice, and was significantly less in TNAP-/- cells than in TNAP+/+ cells at 14 days. Moreover, NTPPPH activity was significantly lower in MV fractions derived at days 10-13 from TNAP-/- mice in comparison to MV fractions from osteoblasts of TNAP+/+ animals, with the values for MV fraction NTPPPH activity being intermediate for TNAP+/- osteoblasts. Despite the presence of the lowest MV fraction NTPPPH specific activity, it was in the TNAP-/- state that the highest MV fraction-associated concentration of the mineralization inhibitor PPi was observed.

Over-expression of the wild-type TNAP cDNA in the MC3T3-E 1 osteoblastic cell line directly promoted an increase in MV fraction NTPPPH specific activity (see below). Moreover, TNAP-expressing primary calvarial osteoblasts ultimately produced MV fractions with significantly more NTPPPH activity than MV fractions produced by TNAP-deficient osteoblasts. Our results indicated that TNAP, by an enzyme activity-dependent mechanism, acts to control mineralization in part by modulating the content of its own inhibitor in osteoblasts and osteoblast-derived MVs. It will be of interest to determine if modulation of PPi concentration at a specific location is a regulatory signal for PC-1 gene expression or the distribution of PC-1 to the plasma membrane and MVs.

Example 9

PC-1 and TNAP are Mutual Antagonists in Mineralization

Although TNAP is essential for bone mineralization, the central mechanism for TNAP action has not been clearly defined (Henthorn et al., "Acid and alkaline phosphatases," In: *Principles of Bone Biology*, eds. Seibel et al., Academic Press, pp. 127-137, 1999). We have assessed whether TNAP, which has multiple enzyme activities (including PPi hydrolysis), could directly antagonize PC-1 action in osteoblasts. We isolated calvarial osteoblasts from two-day old TNAP null mice and cultured the cells in αMEM in mineralizing conditions (50 µg/ml ascorbate, 10 mM β-glycerophosphate for 14 days). Calvarial osteoblasts formed bone nodules, but nodules from the TNAP null mice did not mineralize. We also observed that ATP-dependent Ca precipitation was decreased in calvarial osteoblast MV fractions from TNAP−/− mice.

Confocal immune-microscopy revealed that PC-1, but not the NTPPPH isozyme B10 co-localized with TNAP in osteoblast MV fractions and the pericellular matrix. B10 remained intracellular in these cells, as had been observed in chondrocytes (Johnson et al., *J. Bone Miner. Res.* 14:883-892, 1999; Johnson et al., *Arthritis Rheum.* 42:1986-1997, 1999). PC-1 but not B10 increased MV fraction PPi, and inhibited Ca precipitation by MVs (Johnson et al., *J. Bone Miner. Res.* 14:883-892, 1999; Johnson et al., *Arthritis Rheum.* 42:1986-1997, 1999). TNAP directly antagonized inhibition by PC-1 of MV-mediated $^{45}$Ca precipitation through modulation of MV PPi content. Furthermore, the PPi content of MV fractions was greater in cultured TNAP−/− than TNAP+/+ calvarial osteoblasts. Interestingly, as will be described in detail below, transfection with wild-type TNAP cDNA significantly increased osteoblast MV fraction NTPPPH. Specific activity of NTPPPH also was two-fold greater in MV fractions of osteoblasts from TNAP+/+ mice relative to TNAP−/− mice. Thus, TNAP co-localizes with PC-1 and attenuates PC-1-induced PPi generation that would otherwise inhibit MV-mediated mineralization by osteoblasts. TNAP also regulates PC-1 expression and NTPPPH activity in osteoblasts, suggesting that low PPi levels might have a stimulatory role in the expression of PPi-generating NTPPPHs.

Example 10

Matrix Vesicles (MVs) from TNAP ko Mice Show Increase Levels of PPi and Reduced PC-1 Activity while Overexpression of TNAP Leads to Enhanced Activity of PC-1

Our results revealed that TNAP and PC-1 were co-expressed and co-localized in mineralizing osteoblastic cells and their MV fractions and pericellular matrix. Thus, we assessed the relationship between TNAP and PC-1 functions in MV fractions. To do so, we first transfected MC3T3-E1 cells with cDNAs encoding wild-type TNAP and a catalytically inactive mutant of TNAP, i.e., [R54C]TNAP. Transfection of wild-type TNAP significantly elevated cell-associated and MV fraction-associated TNAP activity in MC3T3-E1 cells and decreased the PPi associated with MV fractions derived from MC3T3-E1 cells transfected with PC-1. Paradoxically, transfection of wild-type TNAP was associated with a significant increase in cell-associated NTPPPH, and an even greater increase in MV fraction-associated NTPPPH activity in MC3T3 cells (FIG. 4A), but no significant change in activity of transglutaminase activity, which served as a control enzyme for these experiments.

Because TNAP appeared to regulate the NTPPPH activity of osteoblastic MC3T3-E1 cells, we assessed whether this effect was dependent on TNAP enzymatic activity. Wild type TNAP, but not the enzyme-inactive mutant of TNAP, induced an increase in both MV fraction NTPPPH and AP activity. In contrast to wild type TNAP, the mutant TNAP failed to decrease MV fraction PPi. More recently we have been able to examine TNAP levels in PC-1−/− cells and found that they show a 50% reduction in TNAP activity compared to littermate control cells.

Example 11

Pathologic Calcifications in PC-1 Deficient Mice and Humans

In long bones of wild-type mice, PC-1 is expressed in osteoblasts, osteocytes, chondrocytes in articular hyaline and meniscal cartilages, and in periarticular and intra-articular ligaments. In growth plates, PC-1 is best detected in epiphyseal regions in late hypertrophic chondrocytes in the calcifying zone, a region in which "trans-differentiation" to osteoblasts may occur. PC-1 also is strongly expressed at entheses (e.g., sites of insertion of intra-articular ligaments, and the junction of synovial membrane with periosteum). In addition, perispinal ligaments are markedly calcified with amorphous calcium phosphate, the mineral phase seen during active bone formation. Calcification is particularly intense around intervertebral disks, where there is an unrestrained regenerative osteoblastic hyperplasia of the periosteum.

Generation of mice with homozygous disruption of the PC-1 gene was as previously described (Sali et al., *Proceedings of the Second International Workshop on Ecto-ATPases and Related Ectonucleotidases*, 1999, Diepenbeek, Belgium, Shaker Publishing BV, Maastricht, Netherlands) In brief, a targeting vector in which a reversed orientation neomycin resistance cassette disrupted exon 9 was introduced into W9.5 embryonal stem cells (of 129/Sv origin) by electroporation, and transfectants selected by growth in the neomycin analog G418 and ganciclovir. Cell lines were maintained in leukemia-inhibitory factor containing medium with neomycin-resistant embryonic fibroblast feeder cells to prevent differentiation, and clones in which the vector had integrated by homologous recombination were identified by Southern blotting. Production of chimeric mice and testing for germline transmission by mating with 129/Sv and C57BL/6 mice was as described (1). Heterozygous offspring were intercrossed to generate homozygous null mutants, and were shown to be totally negative for PC-1 expression by immunohistochemical staining. Reverse transcriptase-PCR and DNA sequencing demonstrated that the PC-1 mRNA was disrupted in precisely the expected location. Backcrossing was continued for more than 10 generations onto C57BL/6 and 129/Sv backgrounds. There was no detectable difference in phenotype between the background strains, and none between male and female mice. In this study, we used mice on the 129/Sv background.

To determine the genotype of each breeder and of progeny, genomic DNA was isolated from tails and from cultured primary osteoblasts, respectively, and analyzed by PCR using a 3-primer PCR protocol for PC-1 null mice. Primers to specifically amplify the targeting region in the wild type PC-1 genomic DNA sequence were: 5'-CCC TTT GTG GTA CAA AGG ACA G-3' (SEQ ID NO:4); and 5'-GCA TGA CCC ATT ATA CAC TTT GT-3' (SEQ ID NO:5); the primer for the targeting vector PGK-PolyA was 5'-GGG TGA GAA CAG AGT ACC TAC-3' (SEQ ID NO:6). Using these three primers, the PCR reaction generated distinct products (1.2 kb for the PC-1 null allele, and 750 bp for the wild type PC-1 allele. Initial Southern blotting assays were used to confirm the reproducibility of the PCR screening for PC-1 null, heterozygotic and wild type genotypes.

The PC-1 knockout mice demonstrated abnormal development of cartilage and bone at sites where PC-1 is normally distributed. There is extension of endochondral growth plates, and progressive ossific fusion of synovium and the lateral edges of growth plates. There is calcification of fibrocartilages, knee cruciate ligaments, and the Achilles tendon. Thus, PC-1 expression by osteoblasts, chondrocytes and ligament fibroblasts modulates skeletal cell differentiation and mineralization. Mice deficient in PC-1 develop both periarticular and arterial apatite calcification in early life. PC-1 null mice serve as a useful model for human Idiopathic Infantile Arterial Calcification (IIAC), in which there is hydroxyapatite deposition with concomitant stenosing smooth muscle cell proliferation in large arteries by early infancy, and dense periarticular calcifications of wrists and ankles (Rutsch et al., 2000).

Paradoxically, even though the PC-1 null mice hyperossify they are osteopenic. The disorganized trabecular architecture may result from widespread hypercalcification of the matrix of the marrow and the disorganized bone architecture contributes to the osteopenia in trabecular bone. In order to assess the degree of rescue of this bone marrow pathology in our cross-breeding experiments, breeding with the TNAP ko mice have been initiated and we have obtained double heterozygous mice (TNAP+/−; PC-1+/−).

Example 12

Effects of Wild-Type and Mutant ANK Protein on Intracellular PPi in Osteoblasts

The ank/ank mouse colony employed in this study was on a hybrid background (derived originally from crossing a C3H and C57BL/6 hybrid male with a BALB/c female). ANK genotypes were analyzed by PCR as previously described (Ho et al., *Science* 289:265 (2000)). Heterozygote breeders were employed to generate and study the distinct litters containing PC-1 null and ank/ank mice and their respective heterozygotic and wild type littermates.

The ank/ank mutant mice develop phenotypic abnormalities remarkably similar in timing, localization and extent to those manifested by the PC-1 null mice. Using primers designed from the newly cloned ank gene (5' primer: 5'-GGA GGG TTG CCG CTG TGA CT-3' (SEQ ID NO:7) and 3' primer 5'-GAT GCC GTG CGA CTC TGG ATA C-3' (SEQ ID NO:8) we were able to detect ank mRNA both by RT-PCR and by RNase protection assays in primary osteoblasts and in MC3T3-E1 cells.

Studies of ank/ank mice ligament fibroblasts (Ho et al., *Science* 289:265-270, 2000), have shown that PC-1 was expressed in these cells but that there was an approximate 50% decrease in extracellular PPi, and only a 15% decrease in specific activity of NTPPPH relative to ligament fibroblasts from normal littermate mice. Furthermore, transfection of wild-type ANK cDNA in littermate normal fibroblasts increases extracellular PPi but it does not do so in ank/ank fibroblasts; thus, PC-1 and ANK may act through a similar or shared pathway (through PPi released to the exterior of the cell) to maintain extracellular PPi at a homeostatic level that suppresses matrix calcification. Inducing a loss of function of either PC-1 or ANK would similarly serve to improve the phenotype of TNAP deficiency, and vice versa for PC-1 and ANK deficiency. Transfection of intact ANK cDNA also increases TNAP activity. This elevation of TNAP activity upon introduction of wt ANK is similar to the induction in TNAP observed when transfecting PC-1 into these cells and further supports the contention that the pathways of production and breakdown of PPi are coordinated. Using three antibodies against ANK, we have been able to detect ANK in normal human SaOS-2 osteoblastic cells and in chondrocytic cells (TC28 immortalized rib chondrocytes, and normal human articular chondrocytes). Transfection of wild-type ANK cDNA into normal mouse calvarial osteoblasts decreased intracellular PPi while transfection of mutant (truncated) ANK increased intracellular PPi as expected based on Kingsley's data using mouse fibroblasts.

Example 13

PC-1 Deficiency and TNAP Null Phenotypes are Mutually Rescued by Cross-Breeding

Inactivation of TNAP results in an increased accumulation of PPi inside the matrix vesicles and in the extracellular matrix surrounding the matrix vesicles. Furthermore, transfection of TNAP into primary osteoblastic cell lines decreases the basal levels of PPi in the matrix vesicles, which is consistent with the specific and dominant function of TNAP in bone, namely to degrade PPi (a potent inhibitor of mineralization) while concomitantly producing free inorganic phosphate (Pi) to promote hydroxyapatite deposition. The availability of the TNAP knockout mice, as well as mice deficient in molecules that appear to converge on this pathway of regulation of PPi levels, makes it possible to verify the role of TNAP and clarify its basic mechanism. Our analysis of the PC-1 knockout mice indicates that the absence of PC-1 leads to a decreased concentration of intracellular and extracellular PPi levels as well as a decrease in PPi inside the matrix vesicles. PPi inhibits crystallization of calcium phosphate from solution, slows the transformation of amorphous calcium phosphate to its crystalline form and slows the aggregation of seed crystals into larger clusters. Thus, a central function of PC-1 is to maintain a high enough level of PPi inside the matrix vesicles to help regulate the rate of intramembraneous formation of apatite crystals and to, thereby, control the first phase of crystal formation in the matrix vesicles.

In these experiments we examine the consequences of generating a double gene knockout by breeding the TNAP ko to the PC-1 ko mice. Maintaining one active allele of PC-1 in a TNAP null background allows a sufficient reduction in intracellular and extracellular PPi so that mineralization is less impaired compared to the TNAP null mice. Similarly, by maintaining one active TNAP allele in the PC-1 null background, the reduction of 50% or more of TNAP activity is sufficient to decrease the rate of degradation of PPi in the extracellular fluid and therefore ameliorate the hyperossification in the PC-1-deficient mice. We have shown that primary osteoblasts derived from TNAP+/− mice delay in vitro mineralization compared to wild-type osteoblasts (Wennberg et al., *J. Bone Mineral Res.* 15:1879 (2000)). Thus, even a limited reduction in TNAP levels can affect the levels of mineralization.

Basal parameters are established in the TNAP and PC-1 null mice bred in the same genetic background, i.e., 129J. We have completed a characterization of the osteoblast and matrix vesicles in the TNAP knockout mice (Wennberg et al., 2000) and a similar characterization is performed for the PC-1 null osteoblasts and matrix vesicles. Calvarial osteoblasts from the PC-1 null mice as well as heterozygous and littermate controls are placed in culture and examined for their ability to deposit bone mineral as measured by von Kossa staining, calcium determinations, TNAP and NTPPPH activities. ANK levels are determined by Western blot analysis. The degree of differentiation of calvarial osteoblasts is assessed by measuring the mRNA for osteopontin, osteocalcin, collagen type I, core binding factor a1 (Cbfa 1), N-cadherin, Smad 5 and 7 as we have done previously (Wennberg et al., *J. Bone Mineral Res.* 15:1879 (2000)). However, rather than using RT-PCR which is semiquantitative at best, we have now optimized the protocols to assay each of these mRNAs, as well as TNAP, PC-1 and ank mRNA, by RNAse protection assays. To examine more detailed changes in the matrix vesicles and bone forming cells such as osteoblasts, and chondrocytes, the bone tissues are fixed with 2% glutaraldehyde-2% paraformaldehyde in cacodylate buffer, and decalcified with 12.5% EDTA in water. The sections are prepared with a standard protocol for transmission electron microscopy.

The osteoblast cultures are also subjected to x-ray diffraction to observe the presence of calcium mineral deposits inside the matrix and in the extracellular fluid using β-glycerophosphate as well as ATP as a substrate. This is particularly important since PC-1 is believed to function specifically as an ATP hydrolase in bone. Cultures are established in 150-mm culture plates, grown for 48 h in growth medium, and then switched to growth medium supplemented with either phosphate, β-glycerophosphate or ATP. Cultures are then incubated for a further 72 h with fresh media changes every 24 h. After aspirating the medium and washing with PBS, the cell layers are scraped, washed in ice-cold ammoniated Nanopure water, and pelleted by centrifugation. The pellets are washed three times with 70% ethanol and lyophilized prior to analysis. X-ray diffraction patterns are then recorded at the Burnham Institute with a Rigaku x-ray Diffractometer equipped with a graphite monochromator calibrated to CuKo radiation ($\lambda=0.154$ nm). A scintillation counter detector coupled to a linear ratemeter is used for data collection. These conditions, allow the discrimination between amorphous calcium phosphate deposits, hydroxyapatite deposits or calcium pyrophosphate dihydrate deposits. These same examinations are performed on the cross-bred partially rescued, [TNAP+/−; PC-1−/−] and [TNAP−/−; PC-1+/−] mice, and double knock-out [TNAP−/−; PC-1−/−] mice if they survive to term. If the homozygous double knockout mice do not survive and die as embryos we perform histopathology on the recovered embryonic tissues.

A thorough histopathological examination, is performed as was done for the TNAP ko mice (Narisawa et al., *Dev. Dynamics* 208:432-446, 1997). The bone tissues are fixed with 10% formalin and decalcified with 0125M EDTA-10% formalin solution, and processed for paraffin embedding. Sections are then stained with hematoxylin and eosin, and the morphology of the cross-bred TNAP×PC-1 ko mice is compared with the tissues of the single gene knock-outs and wild-type control mice. Tissues of other organs, embryos and early postnatal animals are also examined. In vivo parameters such as bone mineral density are measured by dual X-ray absorptiometry (DXA). We also look at routine laboratory parameters in the blood of these cross-bred mice and compare them to basal values in the single ko mice and littermate wild-type controls, e.g., parameters of liver function and number of blood cells. A known condition to exist in hypophosphatasia is myelophtisic anemia and we have observed a 58% reduction in white blood cells in TNAP ko mice. We determine whether this particular aspect of the disease is corrected or not by cross-breeding to PC-1 ko mice. Both TNAP (Marquez et al., *J. Immunol.* 142:3187-3192, 1989) and PC-1 (Goding and Shen, *J. Immunol.* 129:2636-2640, 1982) have been found expressed in the B cell lineage. The PC-1 ko mice have normal leukocyte numbers and leukocyte differentials but abnormal foci of spontaneous apatite deposition as well as decreased trabecula formation in the bone marrow, as reflected by osteopenia despite ligamentous, synovial and cartilagenous hyperminaralization. We pay particular attention to the bone marrow to discern any significant change in the cross-bred mice. These crossbreeding experiments provide fundamental answers as to the mutual degree of correction of the TNAP and PC-1 abnormalities and produce valuable double knock-out cells to work with in vitro.

Example 14

The Bone Abnormalities in the TNAP Null Mice are Rescued by Cross-Breeding to ank/ank Mice The phenotypic abnormalities of the ank/ank mutant mice are surprisingly similar to those of the PC-1 knockout mice. They show a generalized progressive form of arthritis, progressive ankylosis, accompanied by increased mineral deposition, bony outgrowths and joint destruction. However while the phenotypic abnormalities appear to overlap, the mechanism is likely to be different. The ANK molecule causes progressive ankylosis by interfering with the extravesicular step, or phase II, of bone mineral deposition. The ANK protein has been shown to be a transmembrane protein which most likely functions as a component of a PPi transporter, shuttling PPi from inside the cell to the outside extracellular fluid. Notably in the ANK-deficient mice intracellular PPi levels are increased to twice the normal levels while extracellular PPi levels are reduced three to five fold. Thus it appears that a normal function of the ANK protein is to transport PPi to the outside of the cell to be able to regulate the rate of bone mineral deposition in the extra cellular fluid affecting the second phase of mineralization. Thus, the presence of one functional ank allele in a TNAP−/− background is expected to lead to even higher levels of intracellular and intravesicular PPi so as to prevent initial bone mineral deposition. Therefore we expect these mice, if they are born, to show defects in mineralization already at the neonatal or fetal stage compared to 6-10 days of age as in the case of the TNAP null mice. The converse predictions for maintaining one wild-type TNAP allele in the ank/ank mice is similar to the expected outcome of the PC-1 cross-breeding experiments and we expect that we could ameliorate the ankylosis phenotype also in the [TNAP+/−; ank/ank] mice.

Experimentally we proceed as with the analysis of the TNAP×PC-1 TNAP double knockout mice. We comparatively examine the matrix calcifying activities of osteoblasts and their isolated matrix vesicles from ANK-deficient (ank/ank) mice mice that are cross-bred to produce ANK deficient mice on a TNAP wild type, TNAP heterozygote or TNAP null background. Here, mouse osteoblasts that we generate (including single and double TNAP null and PC-1 null cells and their matrix vesicles) serve as critical controls. Calvarial osteoblasts from the ank/ank mice as well as heterozygous and littermate controls are placed in culture and examined for their ability to deposit bone mineral as measured by von Kossa staining, calcium determinations, TNAP and NTPPPH activities and ANK protein size by Western blot analysis and ank mRNA levels by RNase protection assays. The degree of differentiation of calvarial osteoblasts is assessed as described above. Electron microscopy studies, X-ray diffraction studies, bone density measurements and histopathological analysis are performed as described for the TNAP×PC-1 cross-breeding experiments.

Example 15

Levels of Intracellular and Extracellular PPi are Central Regulators of the Expression of the Genes that Regulate PPi Production, Degradation and Secretion (i.e., PC-1, TNAP, and ANK)

It appears clear from the description of the phenotypic abnormalities of the TNAP null, PC-1 null and ANK mutant (ank/ank) mice that the function of these three molecules converge on a pathway regulating intracellular and extracellular PPi levels. Introduction of enzymatically active (but not inactive) TNAP cDNA into an osteoblastic cell line induces NTPPPH activity due to specific induction of PC-1. The reduction of TNAP activity in the TNAP knockout osteoblasts is followed by a reduction in PC-1 levels. Furthermore, two different manipulations that elevate extracellular PPi, i.e., transfection of either PC-1 cDNA or wild-type ANK cDNA, induce TNAP activity in normal fibroblasts.

These results suggest that both PC-1 and ANK either directly or indirectly regulate TNAP expression and that TNAP is also able to regulate PC-1 expression. Our data have not suggested a physical interaction between TNAP and PC-1. Thus, we predict that TNAP regulation by PC-1 and ANK is mediated by extracellular PPi, which in turn is known to be regulated in the same manner by physiologic PC-1 and ANK function. We also predict that ANK and PC-1 expression levels are regulated by PPi. A significant precedent for the contention that a small metabolite such as PPi can up-regulate gene expression is the recent demonstration that the TNAP-derived byproduct of PPi hydrolysis, inorganic phosphate (Pi), induces the osteoblast protein osteopontin (Beck et al., *Proc. Natl. Acad. Sci. U.S.A.* 97:8352-8357, 2000).

As described above, PC-1 is a nucleotide triphosphate pyrophosphate hydrolase which utilizes ATP as the major substrate to generate PPi. However, TNAP, which co-localizes with PC-1, is able to hydrolyze ATP to produce Pi while being affected allosterically by ATP (Pizauro et al., *Biochim. Biophys. Res. Acta* 1368:108-114, 1993) and being subjected to competitive inhibition by the product of this reaction, i.e., Pi. So the relative levels of PPi to Pi in the extracellular matrix are likely to also regulate the kinetic behavior of these two enzymes which are responsible for their production.

Excess intracellular PPi has a variety of toxic effects in prokaryotic and eukaryotic cells (Rachow and Ryan, *Rheum. Dis. Clin. N. Am.* 14:289-302, 1988). These include suppression of DNA replication and of biosynthetic reactions (Rachow and Ryan, *Rheum. Dis. Clin. N. Am.* 14:289-302, 1988), and possible inhibition of the ras growth factor pathway, as suggested via the ability of certain PPi analogue bisphosphonates to induce growth arrest and apoptosis in osteoclasts (Luckman et al., *J. Bone Mineral Res.* 13:581-589, 1998). Thus, a highly evolutionarily conserved protein, inorganic pyrophosphatase (iPPase), is expressed in the cytosol to regulate intracellular PPi (Fairchild and Patejunas, *Biochem. Biophys. Res. Acta* 133-136, 1999). Intracellular PPi levels are likely to be affected not only by iPPase but also by the intrinsic pyrophosphatase activity of TNAP (Rezende et al., *Biochem. J.* 301:517-522, 1994) although primarily an ectoenzyme, TNAP would be expected to exert its predominant effects on intracellular PPi within the lumen of organelles and not within the cytosol. However, some publications have also localized TNAP in mitochondria, so an intracellular role for TNAP cannot be ruled out apriori (Sasaki and Fishman, *Cancer Res.* 33:3008-3018, 1973; Tokumitsu et al., *Histochemistry* 73:1-13, 1981). We examine and compare the kinetic properties of PC-1, TNAP and iPPase in vitro using ATP and PPi as single substrates as well as in mixtures of ATP, PPi and Pi that mimic those concentration found in vivo and in vitro osteoblast cultures derived from wild-type mice, TNAP null, PC-1 null and ank/ank mutant mice and the mutually rescued cross-bred strains in order to demonstrate the relative contributions of these enzyme pathways in determining intracellular and extracellular levels of PPi.

We first establish basic parameters using whole calvarial tissues and cultured calvarial osteoblasts from PC-1 null mice, ank/ank mice and their respective normal littermates as we have done for our TNAP ko mice in order to be able to evaluate the changes observed in the cross-bred, rescued mouse tissues. MVs are isolated by differential ultracentrifugation from whole calvarial tissues, pericellular matrix (using collagenase digestion), and conditioned media, as performed before (Johnson et al., *Am. J. Physiol. Regulatory Integrative Comp. Physiol.* 279:R1365-R1377, 2000). We measure intracellular, conditioned media, and MV PPi. We measure conditioned media and MV inorganic Pi via isobutyl alcohol-bases phosphomolybdic acid extraction (Martin and Doty, *Anal. Chem.* 21:965-967, 1949) and endogenous ATP as reported previously (Johnson et al., *Am. J. Physiol. Regulatory Integrative Comp. Physiol.* 279:R1365-R1377, 2000). We assess the activity in MVs (relative to conditioned media and cell lysates) of PC-1, TNAP, ATPase (Hsu and Anderson, *J. Biol. Chem.* 271:26383-26388, 1996) and inorganic pyrophosphatase (Rezende et al., *Biochem. J.* 301:517-522, 1994) and assess how these activities are affected by absence of PC-1 or ANK expression. We test and compare the ability of aliquots of each MV fraction to precipitate calcium in an ATP-dependent manner, using the absence of ATP in the calcification buffer as a control for background activity. The MV calcification assays are performed as described by us in detail (Johnson et al., *Am. J. Physiol. Regulatory Integrative Comp. Physiol.* 279:R1365-R1377, 2000). We also perform quantitative assays of matrix mineral deposition (including alizarin red binding per cellular DNA and measure the dry weight of hydroxyapatite crystals extracted using papain and hypochlorite) (Johnson et al., *J. Bone Miner. Res.* 14:883-892, 1999; Johnson et al., *Arthritis Rheum.* 42:1986-1997, 1999). We also verify the nature of the matrix crystal deposits using X-ray diffraction as described above. To further assess the mechanistic basis for large increases or decreases in matrix calcification regulated by PC-1 or ANK, we study the MVs in situ in matrix of whole calvariae from PC-1 null and ank/ank mice. We use the elctronmicroscopy techniques described above. Quantification of deposited mineral (in the matrix and associated with MVs) are informative regarding the expected predominance of extravesicular (i.e. extra-MV) calcification expected with deficient ANK and PC-1, and compensation by TNAP deficiency.

These cell culture experiments are complemented with enzyme kinetic experiments to define the relative interplay between PC-1 and TNAP in establishing PPi levels using ATP as substrate as well as the relative contributions of TNAP and inorganic pyrophosphatase (iPPase) to the destruction of PPi. One approach is to use antibodies (polyclonal, monoclonal or even anti-peptide antibodies) to trap onto microtiter wells (and, thus, immunopurify in vitro) enzymes from a crude extract, followed by a detailed kinetic analysis under different buffer conditions, pHs, substrates and inhibitors. Examples of this approach can be seen in Hoylaerts et al., 1997 and Manes et al., 1998 (Appendices IX and X). We have developed rabbit and chicken anti-peptide antibodies that bind to mouse TNAP and we anti-PC-1 antibodies. Rabbit polyclonal antibodies are raised to the purified rat iPPase that will also cross-react with mouse iPPase, the mouse inorganic pyrophosphatase (iPPase) is cloned using oligonucleotide primers from the recently published human inorganic pyrophosphatase cDNA (Fairchild and Patejunas, *Biochem. Biophys. Res. Acta* 133-136, 1999), and antipeptide antibodies are developed from the deduced mouse sequence. This provides us with a cDNA to be used in transfections if needed and a second source of antigen for immunization. The specific antibodies to TNAP, PC-1 and iPPase are used to bind and assay specifically each enzyme component, even when they are present in the same mixture (as is the case in extracts from osteoblasts and matrix vesicles). We first determine the relative amounts of each enzyme component by enzyme immunoassays as before (Hoylaerts et al., *J. Biol. Chem.* 272:22781-22787, 1997; Manes et al., *J. Biol. Chem.* 273:23353-23360, 1998). Determining the in situ concentration of Pi, PPi and ATP, as described above, in our osteoblasts cultures and matrix vesicles preparations allows us to assay each enzyme under conditions in which a single substrate is present as well as in the simultaneous presence of more than one substrate at various physiological concentrations. This analysis elucidates the relative efficiency of each of these enzyme components in producing as well as in breaking down PPi. These in vitro studies complement our in vivo analysis of the deficiencies and degree of rescue obtained in the cross-breeding experiments already described.

In order to test the hypothesis that PPi itself represents the signaling molecule that influences the transcription of the TNAP, PC-1 and ANK genes, we examine the levels of TNAP, PC-1 and ANK in calvarial tissue and osteoblasts from the mutant mouse lines and in the rescued mouse strains and by measure mRNA for TNAP, PC-1 and ANK by Northern blot analysis. Subsequently, cells from the different mutant strains and rescued mice are exposed to medium with different concentrations of PPi, or non-hydrolyzable analogues (phosphocitrate and the biphosphonate etidronate), for various time points and tested for changes in mRNA levels of the three genes. In addition, in vitro cytoplasmic and nuclear microinjection of PPi and analogues into osteoblastic cells are performed to examine the effect of intracellular PPi on these same genes. Measurements of mRNA changes are monitored by real-time RT-PCR using an ABI 7700 Sequence Detection system to facilitate these measurements.

These evaluations are done on osteoblastic cells from the different mutant mice and cross-bred strains with or without rescue of the deficient molecule after specifically transfecting the respective cDNAs back into the deficient cells. As a control for the transfections, we employ mutant enzyme-deficient PC-1 (Johnson et al., *J. Bone Miner. Res.* 14:883-892, 1999; Johnson et al., *Arthritis Rheum.* 42:1986-1997, 1999), mutant ANK (Ho et al., *Science* 289:265-270, 2000), and mutant enzyme-deficient TNAP (Wennberg et al., *J. Bone Mineral Res.*, 2000). The table summarizes the experiments to be performed and the results that are expected.

TABLE 1

Predicted results for the experiments in this section. The example used is for wild-type osteoblastic cells. ePPi: extracellular PPi; iPPi: intracellular PPi.

| Source of Osteoblasts | Factor expressed or delivered | Predicted effect on PPi Intracellular Extracellular | Predicted effect on mRNA expression TNAP PC-1 | | ANK |
|---|---|---|---|---|---|
| WildType | TNAP | ↓ ↓ | — | ↑ | ↑ |
| | iPPiase | ↓ = | ↓ | ↑ | ↑ |
| | PC-1 | ↑ ↑ | ↑ | ↓ | — |
| | ANK | ↓ ↑ | ↑ | — | ↓ |
| | ePPi or PPi analogue | = ↑ | ↑ | ↓ | ↓ |
| | iPPi or PPi analogue | ↑ = | ↑ | ↑ | ↓ |

The combination of the in vitro data with the powerful validation provided by the cross-breeding experiments and the ex vivo experiments allow us to understand the mechanisms that control PPi levels and how these levels affect the genes that control its production, degradation and secretion.

Recently some very powerful technologies are becoming available to examine changes in gene expression occurring after a gene deletion, such as DNA arrays or gene chips. These approaches, while representing large scale untargeted screenings for changes, can be very informative (Lee et al., *Science* 285:1390-1393, 1999; Shelton et al., *Current Biology* 9:939-945, 1999; Young, *Cell* 102:9-15, 2000; Lockhart and Winzeler, *Nature* 405:827-836, 2000; Risch, *Nature* 405:847-856, 2000). Affymetrix offers the following gene chips that are useful for this purpose: Murine Genome U74A, U74B and U74C, which altogether contain 30,000 genes. U74A contains only known genes, U74B and U74C chips contain EST sequences. These chips are probed with RNA derived from osteoblast cultures from TNAP, PC-1 and ANK mutant mice and changes in gene expression between these gene defects are evaluated. These basic changes are then compared with the mutually rescued phenotypes using RNA from the cross-bred mouse mutants. Total RNA is extracted with TRIzol reagent, Gibco BRL Life Technology and 1-5 µg total RNA used for double stranded cDNA synthesis. In vitro transcription is used to produce biotin-labeled cRNA from the cDNA using an Enzo BioArray High Yield RNA Transcript Labeling kit. The cRNA is quantified using spectrophotometric analysis and 15 µg of cRNA are fragmented by heat and ion-mediated hydrolysis, the 5'-end RNA termini are enzymatically modified with T4 olynucleotide kinase and gamma-S-ATP and used for probing the chips. The software Genespring (Silicon Genetics, Redwood City, Calif.), is useful for narrowing down the number of candidate genes to a manageable 10 to 30, making it very realistic to follow up the putative candidate gene chip results with Northern blot analysis to confirm the changes. This powerful approach reveals previously unknown molecules that are involved in the pathways of mineralization and is useful for identifying molecules that mediate the effects of PPi on the TNAP, PC-1 and ANK genes.

Example 16

Survival of ttPp and ttpp Mice

The ttPp or ttpp mice survive. We have verified by Southern blot analysis that the genotype of two mice that lived to 25 days of age corresponded to TNAP×PC-1 double homozygote knockout mice. Table 2 shows mice with their corresponding genotypes and life span. Considering the fact that our hypophosphatasia TNAP−/− knockout mice (ttPP in Table 2) do not survive beyond 10-11 days of age, this data clearly indicates that by deleting an antagonist of alkaline phosphatase function we have ameliorated the phenotypic abnormalities of hypophosphatasia and doubled the life span of these mice. This data demonstrates that loss of function of the skeletal TNAP antagonist PC-1 ameliorates TNAP deficiency-associated osteomalacia in vivo.

We also further characterized PC-1 knockout primary osteoblasts in vitro. To stimulate matrix calcification, calvarial cells were cultured in complete αMEM media supplemented with β-glycerophosphate (10 mM) every third day and L-ascorbic acid (50 μg/mL) daily. Primary osteoblasts of PC-1 null mice gradually produce significantly increased calcification of the matrix, as measured by the Alizarin Red S binding assay, relative to the results with wild type cells. (n=6, * p<0.05).

We also examined the NTPPH activity and production of inorganic pyrophosphate (PPi) in these PC-1 knockout primary calvarial cultures. NTPPPH activity and extracellular PPi levels were both decreased by approximately one-half in PC-1 null cells. Thus, PC-1 makes a large (but not a solo) contribution to the total NTPPPH activity in these cells. PC-1 also clearly is a major player in extracellular PPi regulation in calvarial osteoblasts.

TABLE 2

Number, life span and genotype of the offspring born by cross-breeding TNAP +/− and PC-1 +/− mice.
Offspring From TtPp × TtPp breedings

| Genotype | No. of mice born vs (expected) | Days of Survival |
|---|---|---|
| TtPp | 7 (7.8) | > 1 year |
| TTPp | 3 (3.9) | > 1 year |
| TtPP | 3 (3.9) | > 1 year |
| Ttpp | 7 (3.9) | 1 year |
| ttPp | 3 (3.9) | 11-14 days |
| TTPP | 2 (1.9) | > 1 year |
| ttPP | 2 (1.9) | 10-11 days |
| TTpp | 2 (1.9) | 1 year |
| ttpp | 2 (1.9) | 25 days |

Example 17

Rescue of Bone Abnormalities

The Akp2 (TNAP) KO mice initially were hybrids of C57Bl/6×129/J mouse strains while the Enpp1 (PC-1) KO mice were hybrids of C57Bl/6×129/SvTerJ mouse strains. Double heterozygote mice were bred continuously by brother-sister mating into a C57Bl/6 background.

Clear evidence of rescue of osteomalacia in Akp2/Enpp1 double KO mice was observed. The lack of mineralization in the calvaria (shown by Alcian blue staining of the unmineralized osteoid) and the absence of secondary ossification centers in the hind limb phalanges characteristic of the hypophosphatasic mice (Akp2 KO) was corrected in the Akp2/Enpp1 double KO mice. Correction in the length and histological appearance of the growth plates of the double KO mice was also observed. Akp2 KO mice show a characteristic thickening of the hypertrophic zone of the growth plates in the tibia, while the Enpp1 KO mice display a marked thinning and hypocellularity of the corresponding growth plates. Restoration of normal growth plate thickness and cellularity was evident in the Akp2/Enpp1 double KO mice. The lumbar spine of all genotypes exhibited differences in the degree of mineralization in the vertebral epiphyses. The ratio of the number of secondary ossification centers containing visible mineral deposits to those containing no visible deposits was determined. Ten-day old Enpp1 KO mice have precipitated mineral in every lumbar vertebral epiphysis (100%), while in the corresponding areas of age-matched Akp2 null mice mineral deposits are virtually absent (6%). More than half the lumbar vertebrae of the Akp2/Enpp1 double KO mice had mineral deposits, a ratio comparable to that found in the wild-type mice. Each functional allele of Akp2 and Enpp1 contributes to the mineralization status of the spine. Note that even carriers (heterozygotes) of Akp2 and Enpp1 null mutations are affected.

We then examined the ability of Akp2/Enpp1 double KO primary osteoblasts to mineralize bone nodules in vitro. Akp2 null osteoblasts cultured for 21 days precipitated significantly less mineral than wild-type osteoblasts, whereas osteoblasts of Enpp1 null mice precipitated significantly more mineral than control cells. A normal mineralization capacity was restored in the Akp2/Enpp1 double KO osteoblasts. Quantification of the amount of PPi in the MVs isolated from the cultured osteoblasts revealed that MVs from Akp2 KO osteoblasts had increased amounts of PPi, whereas those from the Enpp1 null osteoblasts had decreased levels of PPi. The MVs derived from the Akp2/Enpp1 double KO osteoblasts exhibited PPi concentrations that were comparable to those of wild-type MVs.

The data demonstrate that in osteoblasts, TNAP and PC-1 are central, directly antagonistic regulators of the concentration of the matrix calcification inhibitor PPi. Restoration of extracellular Ppi to normal levels in Akp2/Enpp1 double KO mice, in conjunction with correction of the hypomineralization resulting from the TNAP deficiency, points to the key role of PPi in this phenotypic rescue. The data suggest that the extracellular PPi pool largely determines the rate of hydroxyapatite crystal formation in bone tissue. PC-1 is a major contributor to the extracellular PPi pool whereas the action of TNAP restricts PPi concentration and also contributes to the extracellular Pi pool available for the formation of hydroxyapatite crystals. The concerted action of TNAP and PC-1 ensure that the optimal concentration of PPi is achieved under normal conditions. In hypophosphatasia the PPi pool increases due to lack of TNAP's pyrophosphatase activity and osteomalacia ensues as PPi's inhibition of hydroxyapatite deposition is augmented. In PC-1 deficiency, the extracellular PPi pool decreases due to reduced production of PPi and hypermineralization takes place as PPi inhibition of hydroxyapatite deposition is relaxed. The simultaneous deletion of TNAP and PC-1 correct the levels of extracellular PPi and normal mineralization is re-established.

Example 18

In Vivo Characterization of TNAP and ANK Double Knockouts

As Akp2/Enpp1 double null mice display normal bone mineralization (Hessle et al., *Proc Natl Acad Sci USA* 99:9445 (2002)), a simultaneous deficiency of TNAP and ANK would likely also show the same correction of ossification. Similar to the whole mount skeletal preparations of Akp2/Enpp1 double-KO mice, the Akp2−/−; ank/ank skeletons displayed a correction of the hypomineralization. By counting and determining the ratio of the number of mineralized apophyses in the lumbar spine, we concluded that Akp2 KO mice lacking functional ANK were hypermineralized showing 80% mineralized apophyses compared to the normal 65% (FIG. 3). However, Akp2 KO mice deficient in only one allele of ANK had the same amounts of mineralized apophyses as wt mice (FIG. 3). This indicates that a reduction equivalent to half the functional ANK molecules appears to be sufficient to restore the mineralization capacity to normal levels in conditions of hypophosphatasia As Akp2−/− mice deficient with only one functional allele for ANK had the same amounts of mineralized apophysis compared to those of wild-type mice, only small reductions of ANK function appears to be sufficient to restore the mineralization capacity to normal levels in conditions of hypophosphatasia.

This data clearly indicates that even a limited degree of inhibition of ANK function will lead to an amelioration of the hypomineralization found in hypophosphatasia.

Example 19

Ex Vivo Characterization of TNAP and ANK Double Knockouts

The mineralizing capacity of Akp2−/−; ank/ank osteoblasts was then examined. Briefly, primary calvarial osteoblasts from each respective genotype were cultured in a differentiation media and the mineralization capacity, extra- and intracellular PPi was measured at different time points (FIG. 4).

Figure 4A:
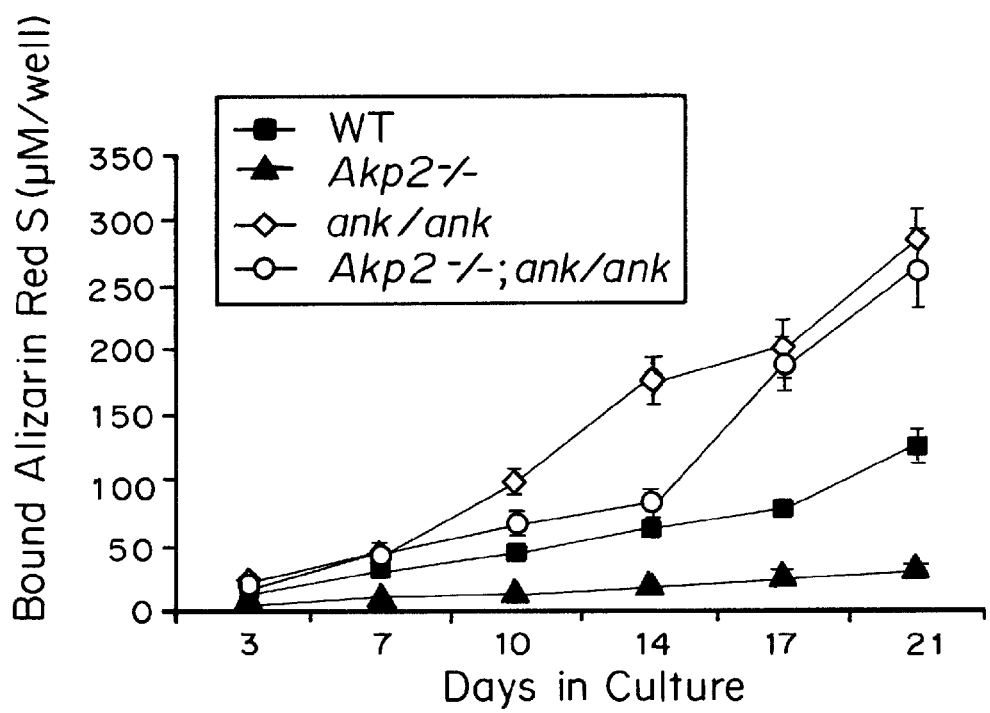
FIG. 4 shows that primary Akp2−/−; ank/ank osteoblasts display a slight correction in the A) hypermineralization and B) extra-cellular and C) intra-cellular PPi levels compared to those of ank/ank osteoblasts.
Figure 4B:
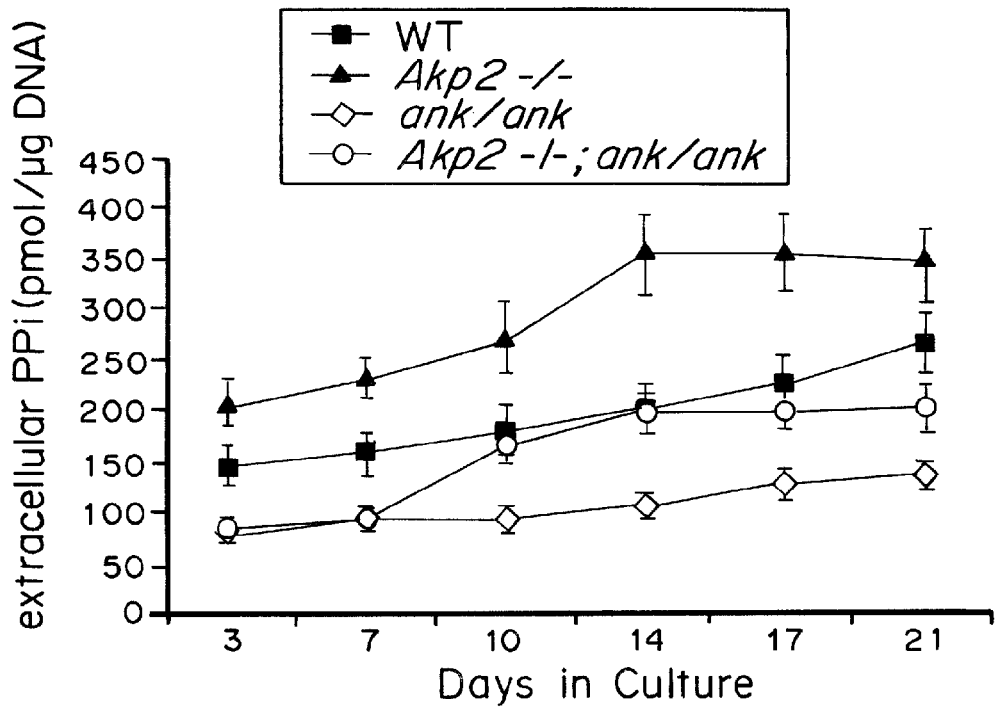

Akp2 KO osteoblasts precipitated significantly less mineral than wild-type cultures, whereas Akp2−/−; ank/ank osteoblasts showed an overall increased ability to mineralize their surrounding matrix compared to wild-type osteoblasts (FIG. 4a). However, double deficient osteoblasts were not as severely hypermineralized as ank/ank osteoblasts lacking only functional ANK protein up to culture-day 17. Thus, the lack of TNAP activity still had a repressing affect on the osteoblastic mineralization of ank/ank cultures during the early to mid stages of culture.

Figure 4C:
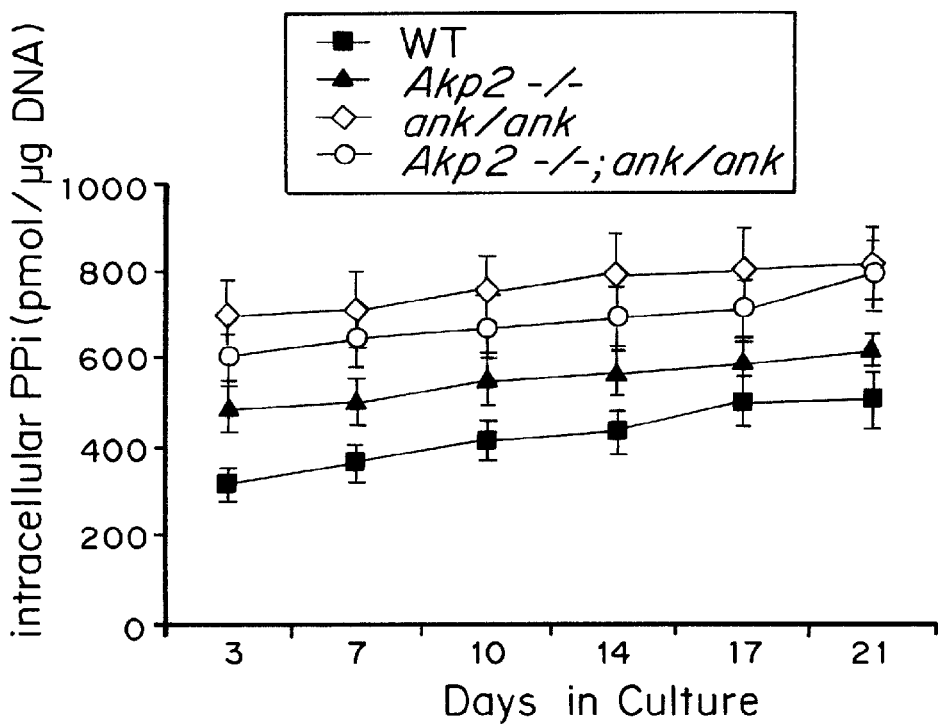

Quantification of extracellular (FIG. 4b) and intracellular (FIG. 4c) amounts of PPi revealed abnormally high levels in Akp2 KO cultures, whereas ank/ank cultures showed reduced matrix and elevated cytosolic concentrations of PPi compared to those of wild-type. In the mid-stages of mineralization, primary osteoblast cultures from Akp2−/−; ank/ank mice displayed normal extracellular PPi levels. However, at early and late time-points of culture the $PP_i$ concentrations were subnormal. The elevated intracellular $PP_i$ levels of Akp2−/−; ank/ank osteoblasts were partially improved compared to those of ank/ank osteoblasts (FIG. 4c).

Example 20

Changes in PPi Levels Lead to Parallel Changes in Osteopontin Levels

Figure 5:
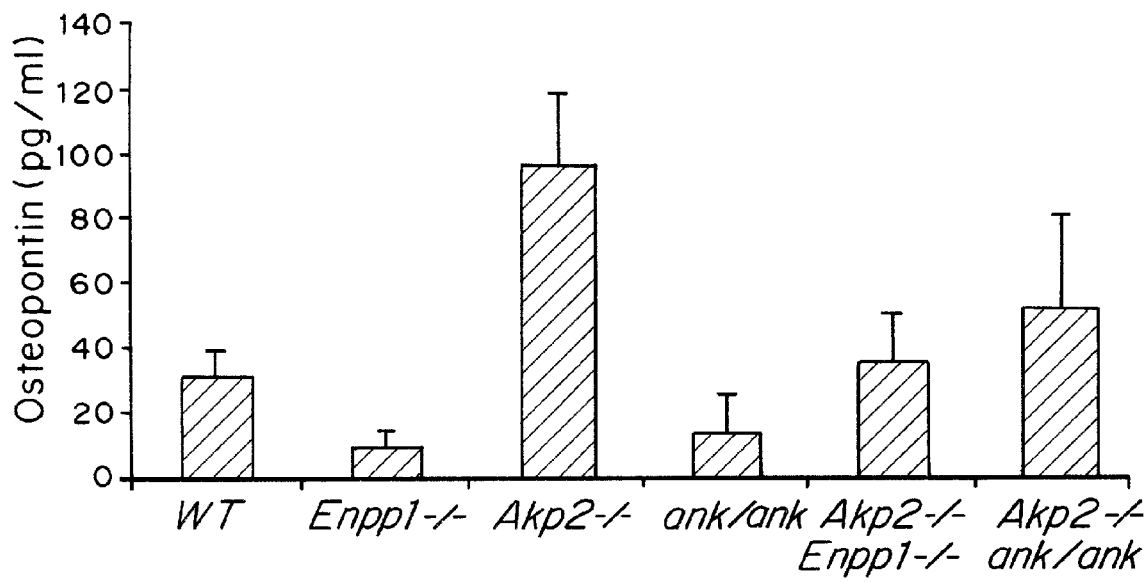
FIG. 5 shows that the change in osteopontin (OPN) levels paralleled the fluctuations observed in extracellular $PP_i$ in each genotype in serum of Akp2, Enpp1 and ANK, single and double deficient mice.

We assessed whether or not the decreased extracellular $PP_i$ levels triggered any alterations in osteoblast-related gene expression. Osteopontin (OPN), osteoprotegerin (OPG), matrix gla protein (MGP) and cbfa1 mRNA expression levels of primary osteoblasts were analyzed by RT-PCR. PC-1 KO and ank/ank osteoblasts had comparable expression patterns of OPG, MGP and cbfa1 to wild-type osteoblasts. However, osteopontin expression was considerably lower in mRNA extracts from both PC-1- and ANK-deficient osteoblasts compared to control cultures. This observed decrease was confirmed at the protein level by ELISA using anti-osteopontin antibodies. Immunohistochemistry of lumbar vertebrae from PC-1 KO mice also revealed a less dominant osteopontin staining pattern compared to those of wild-type. Recently, we tested all single and double deficient mice for their levels of osteopontin (FIG. 5). This analysis revealed an increased concentrations of osteopontin in TNAP KO mice, and mice double deficient in TNAP and PC-1 had normal serum levels osteopontin. Interestingly, all the trends in the amounts of osteopontin accurately reflect the $PP_i$ levels in the extracellular matrix for each mouse genotype.

The down-regulation of osteopontin in PC-1- and ANK-deficient mice was intriguing to us due to the shared properties between osteopontin and $PP_i$. Similar to $PP_i$, osteopontin has the ability to inhibit mineralization by binding to hydroxyapatite crystals and suppresses further crystal propagation (Sodek et al., 2000; Boskey et al., Calcif. Tissue Int. 71: 145-154, 2002). Interestingly, when recombinant osteopontin was added to PC-1−/− or ank/ank osteoblast cultures, their mineralization capacity was restored to normal. Similar correction of matrix calcification was observed when osteoblasts were cultured with recombinant soluble PC-1 protein. However, the addition of soluble PC-1 protein also allowed both the extracellular $PP_i$ and osteopontin levels to rise to close to normal concentrations. In fact, the mere addition of $PP_i$ to osteoblast cultures deficient in PC-1 or ANK protein, corrected their osteopontin expression levels to those comparable to wild-type.

Thus, PC-1 KO and ANK-deficient osteoblasts had similarities in their extracellular $PP_i$ levels, gene expression patterns and ability to calcify the matrix. A comparable disregulation of the mineralization inhibitor osteopontin in both PC-1- and ANK-deficient osteoblasts was also observed. These findings of depressed levels of osteopontin, together with OPN induced expression in the presence of higher concentration of $PP_i$, indicates that $PP_i$ regulates osteopontin expression.

Example 21

Treatment of Ankylosis by in Vivo Inhibition of TNAP Activity

Figure 6A:
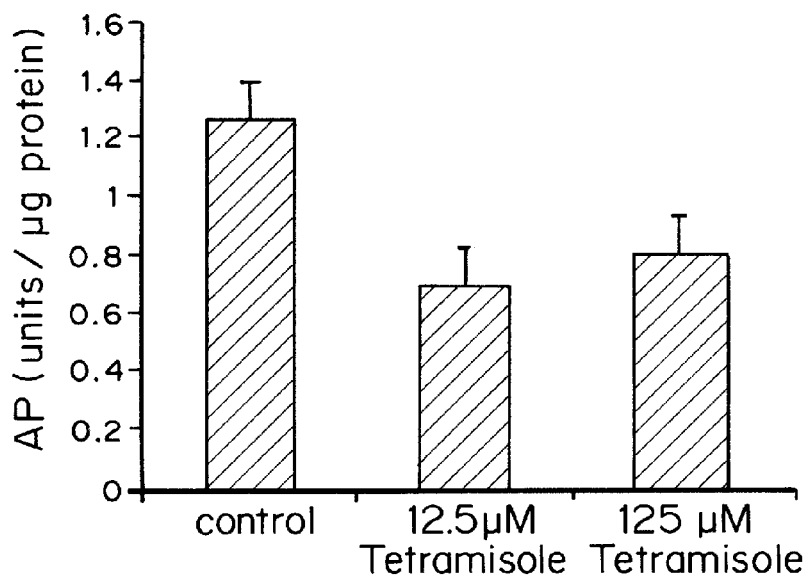
FIG. 6 shows how the TNAP activity A), the extracellular $PP_i$ B) and the mineralization ability C) are effected in cultured wild-type primary osteoblasts treated with tetramisole.
Figure 6B:
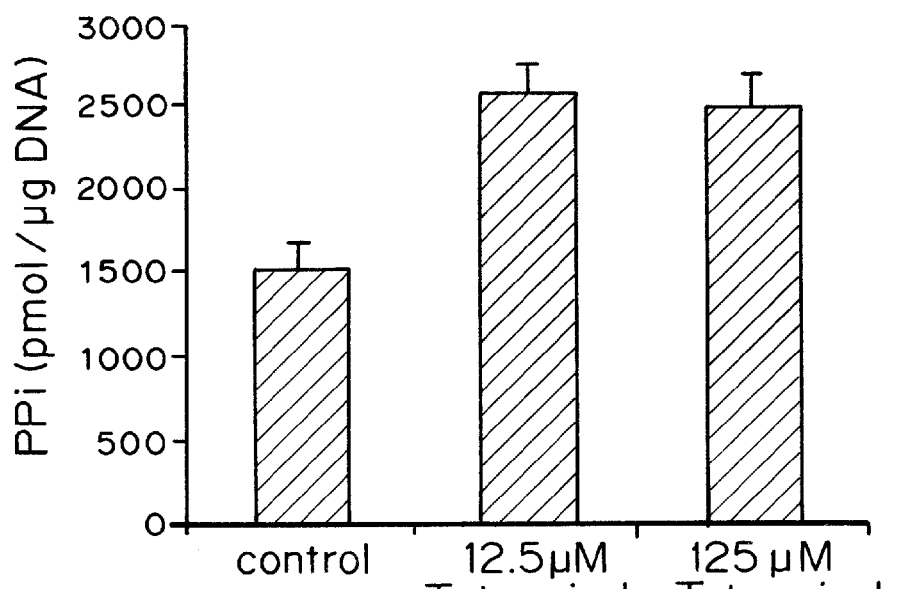
Figure 6C:
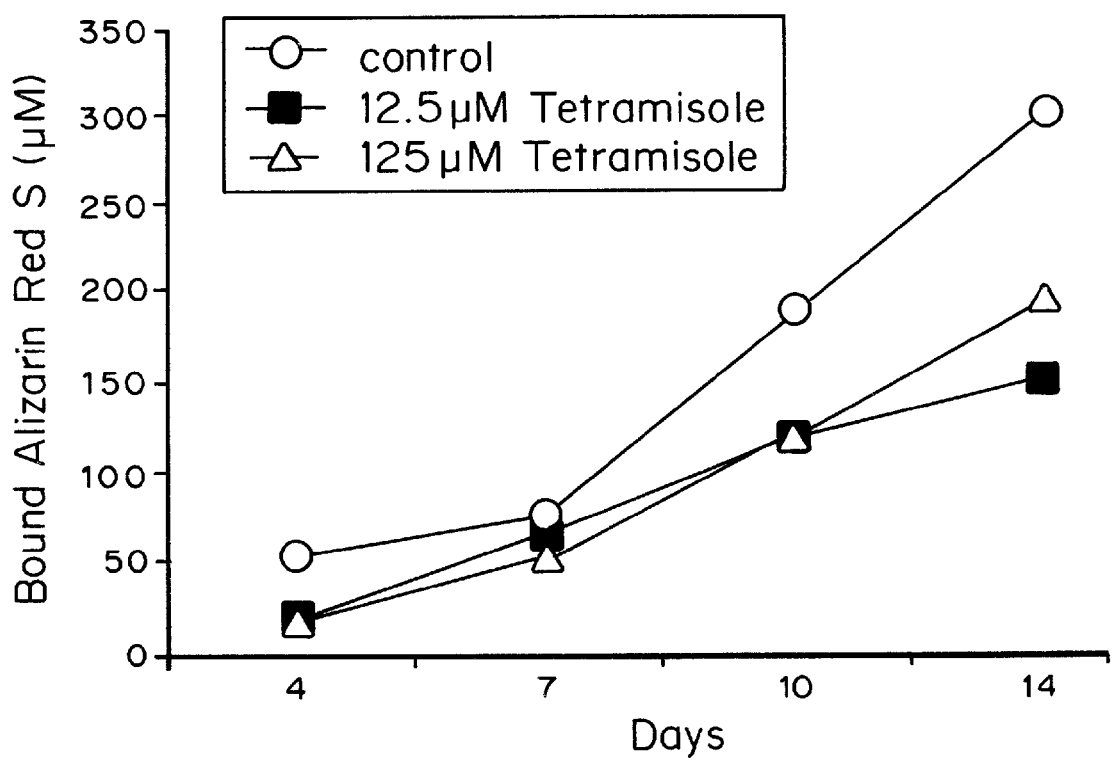
Figure 7A:
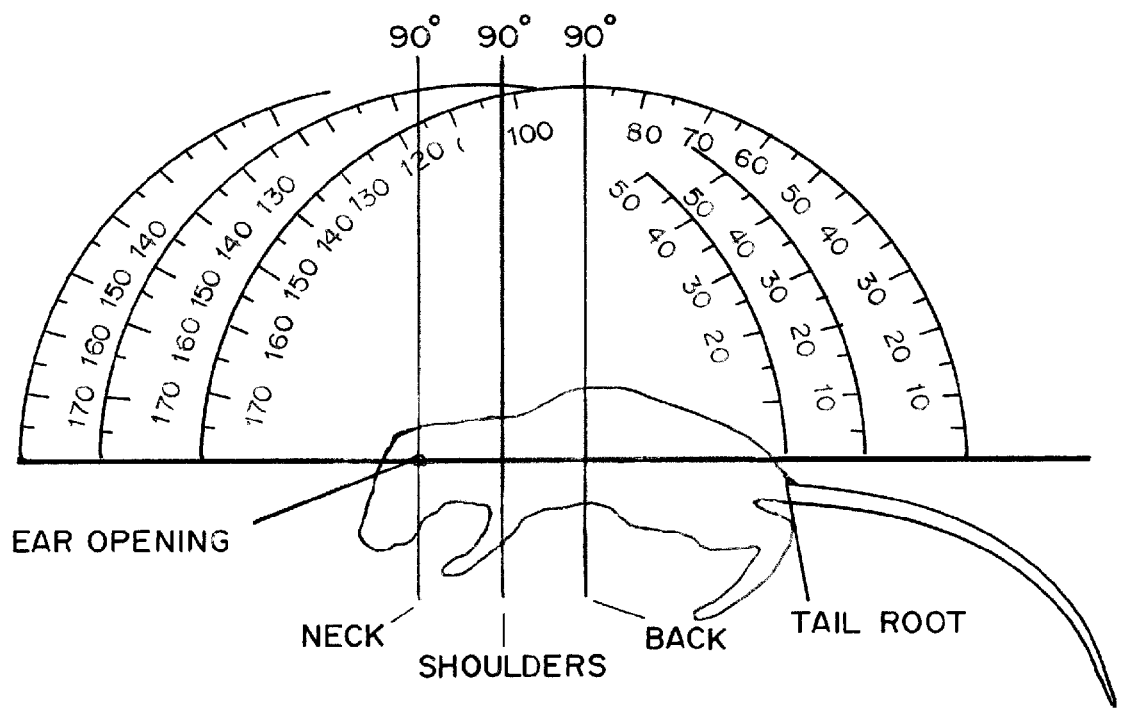
FIG. 7 shows that the Enpp1 KO and ank/ank mice exhibited improvement in their flexibility when treated with tetramisole, an inhibitor of TNAP activity. A) Is a schematic figure showing the method by which the degree of flexibility of the spine was assessed. Histograms display increased flexibility B) from the neck down to the tail root, C) from the shoulders down to the tail root, D) and of the lumbar spine of the treated osteoarthritic mice.
Figure 7B:
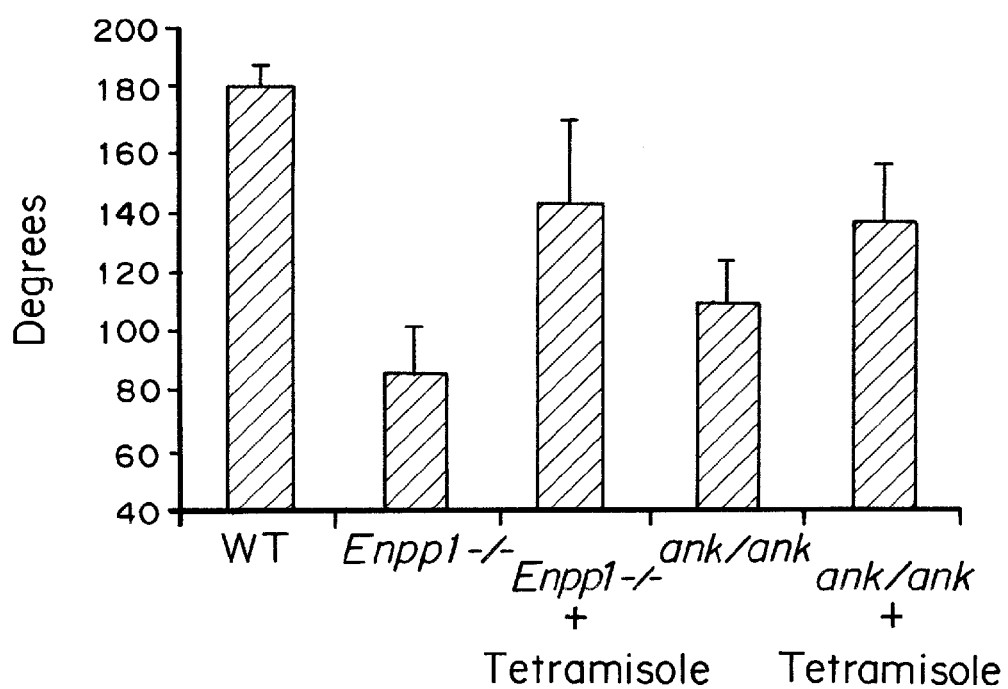
Figure 7C:
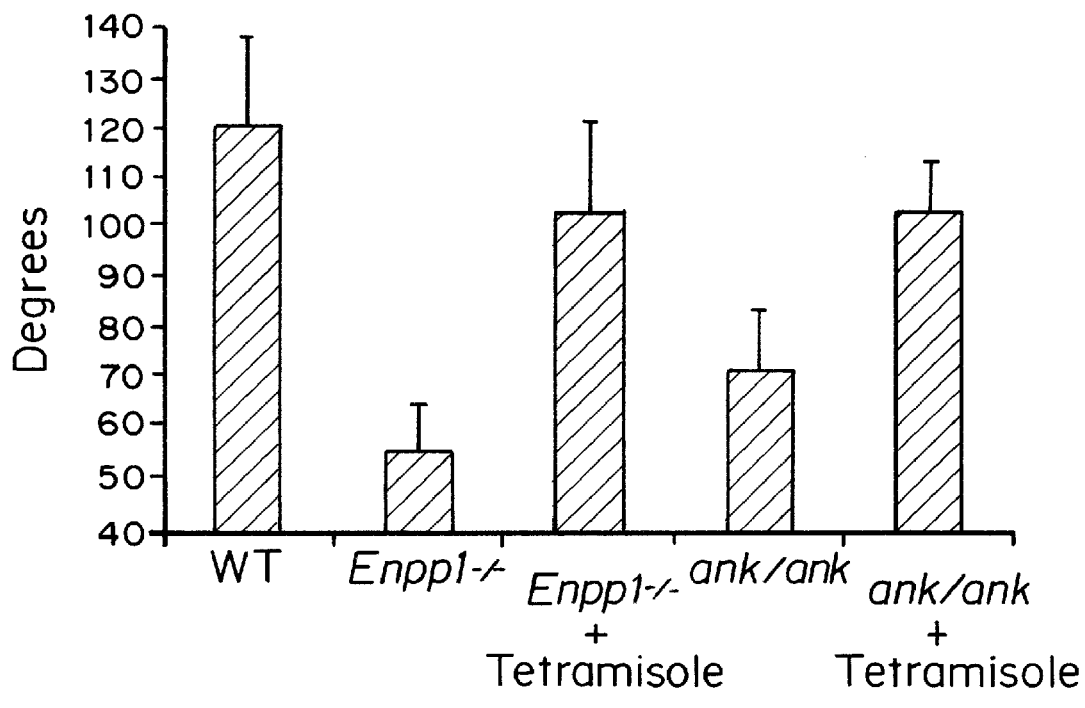
Figure 7D:
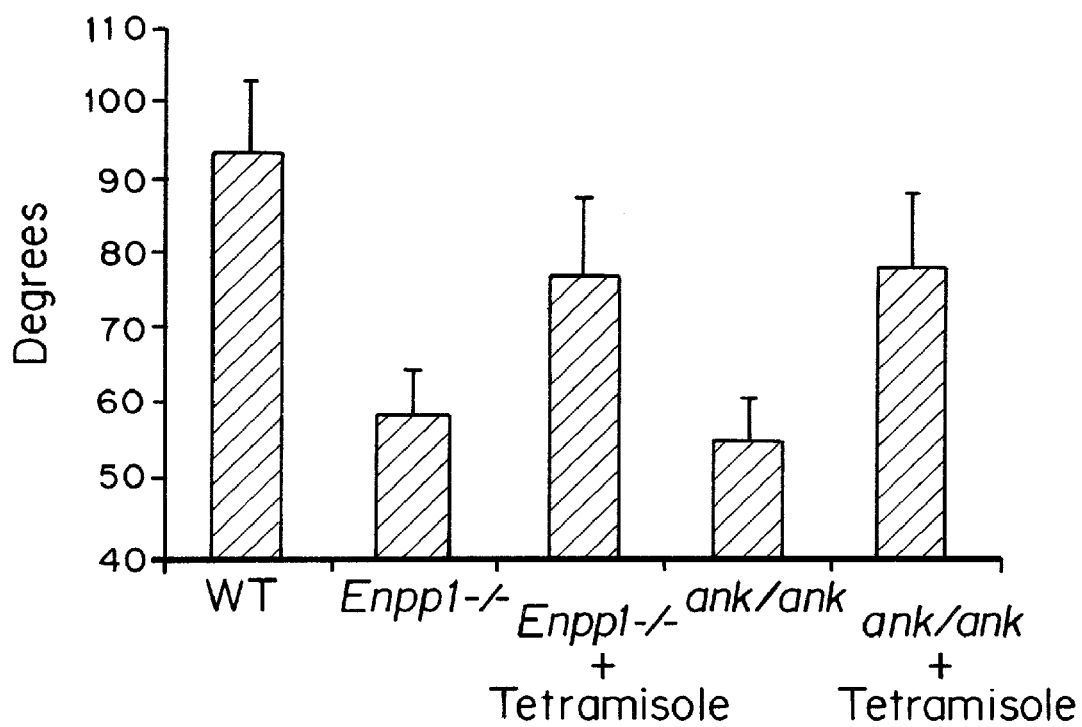

To select a TNAP inhibitor for in vivo use, we measured the efficiencies by which tetramisole, levamisole and L-homoarginine, all specific uncompetitive inhibitors of TNAP activity, were able to suppress TNAP activity, elevate extracellular $PP_i$ levels and inhibit mineralization in the MC3T3-E1 osteoblastic cells line. Tetramisole was chosen due to its higher efficiency in elevating extracellular $PP_i$ levels (FIG. 6).

Briefly, tetramisole (DL-2,3,5,6-tetrahydro-6-phenyl-imidazo-thiazole, Sigma) was delivered subcutaneously into Enpp1 KO and ank/ank mice via ALZET osmotic pumps (Durect Corporation, Cupertino, Calif.) at a dose of 10 μg/g/day. Pumps loaded with tetramisole or PBS were implanted at one month of age and mice were treated for 3 months, with monthly replacements of the pump. At least ten mice from each group were sacrificed at four months for analysis. Following euthanasia, the flexibility of the spine was measured by the degree by which the root of the tail could be pulled back until resistance prevented further flexing.

Enpp1 KO and ank/ank treated mice showed an enhanced flexibility of the spine compared to those of control mice (FIG. 7). Despite the fact that untreated Enpp1 KO mice were less flexible then ank/ank mice, they showed a greater degree of improvement in response to treatment of tetramisole.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method for decreasing matrix mineralization in a tissue of a patient having a disease associated with insufficient or deficient ankylosis protein (ANK) activity or expression compared to normal ANK activity or expression, comprising administering an amount of a tissue non-specific alkaline phosphatase (TNAP) inhibitor selected from the group consisting of L-tetramisole, D-tetramisole, levamisole, dexamisole, L-homoarginine, teophyllin and forphenicine to the tissue or patient effective to inhibit TNAP expression or activity.

2. The method of claim 1 wherein said tissue comprises bone, cartilage or ligament.

3. The method of claim 1 wherein said tissue exhibits undesirable or excessive matrix mineralization.

4. The method of claim 1 wherein said patient is affected by the disease selected from the group consisting of arterial calcification, ankylosing spondylitis, ossification of the posterior longitudinal ligament, myositis ossificans, diffuse idiopathic skeletal hyperostosis, calcific tendonitis, rotator cuff disease of the shoulders, osteomalacia, metabolic bone disease associated with renal failure, bone spurs, cartilage or ligament degeneration due to hydroxyapatite crystal deposition, chondrocalcinosis and osteoporosis.

5. The method of claim 4, wherein one or more symptoms of said disease is reduced.

6. A method of treating a patient having a disease selected from the group consisting of arterial calcification, ankylosing spondylitis, ossification of the posterior longitudinal ligament, myositis ossificans, diffuse idiopathic skeletal hyperostosis, calcific tendonitis, rotator cuff disease of the shoulders, osteomalacia, metabolic bone disease associated with renal failure, bone spurs, cartilage or ligament degeneration due to hydroxyapatite crystal deposition, chondrocalcinosis and osteoporosis, caused at least in part by deficient ANK activity or expression, comprising administering a compound selected from the group consisting of L-tetramisole, D-tetramisole, levamisole, dexamisole, L-homoarginine, teophyllin and forphenicine, wherein the compound reduces expression or activity of TNAP in a tissue of the patient affected by the disease.

7. The method of claim 6, comprising administering to said patient an amount of a TNAP inhibitor effective to reduce one or more symptoms of said disease.

* * * * *